United States Patent
Yang et al.

(10) Patent No.: US 10,285,910 B2
(45) Date of Patent: *May 14, 2019

(54) SUBLINGUAL AND BUCCAL FILM COMPOSITIONS

(71) Applicant: Aquestive Therapeutics, Inc., Warren, NJ (US)

(72) Inventors: Robert K. Yang, Henderson, NV (US); Richard C. Fuisz, Beverly Hills, CA (US); Garry L. Myers, Kingsport, TN (US); Joseph M. Fuisz, Surfside, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/163,029

(22) Filed: Oct. 17, 2018

(65) Prior Publication Data
US 2019/0046411 A1  Feb. 14, 2019

Related U.S. Application Data

(60) Continuation-in-part of application No. 13/853,290, filed on Mar. 29, 2013, now Pat. No. 10,111,810, which is a continuation of application No. 13/052,655, filed on Mar. 21, 2011, now abandoned, which is a continuation of application No.
(Continued)

(51) Int. Cl.
| | |
|---|---|
| *A61K 9/70* | (2006.01) |
| *A61J 3/00* | (2006.01) |
| *B29C 48/08* | (2019.01) |
| *A61K 9/00* | (2006.01) |
| *F26B 13/10* | (2006.01) |
| *F26B 13/20* | (2006.01) |

(Continued)

(52) U.S. Cl.
CPC ............ *A61J 3/00* (2013.01); *A61K 9/006* (2013.01); *A61K 9/7007* (2013.01); *B29C 48/08* (2019.02); *F26B 13/10* (2013.01); *F26B 13/104* (2013.01); *B29C 48/91* (2019.02); *B29C 48/919* (2019.02)

(58) Field of Classification Search
CPC ................................................. A61K 9/7007
See application file for complete search history.

(56) References Cited

U.S. PATENT DOCUMENTS

| 26,401 A | 12/1859 | Brashear et al. |
|---|---|---|
| 307,537 A | 11/1884 | Foulks |

(Continued)

FOREIGN PATENT DOCUMENTS

| AU | 741362 B2 | 11/2001 |
|---|---|---|
| CA | 2274910 C | 7/2005 |

(Continued)

OTHER PUBLICATIONS

Blank, Z. et al., "Structural studies of organic gels by SEM", J. Material Science 9:1815-1822 (1974).
(Continued)

*Primary Examiner* — Benjamin J Packard
(74) *Attorney, Agent, or Firm* — Hoffmann & Baron, LLP

(57) ABSTRACT

The present invention relates to products and methods for treatment of various symptoms in a patient, including treatment of pain suffered by a patient. The invention more particularly relates to self-supporting dosage forms which provide an active agent while providing sufficient buccal adhesion of the dosage form. Further, the present invention provides a dosage form which is useful in reducing the likelihood of diversion abuse of the active agent.

30 Claims, 1 Drawing Sheet

Related U.S. Application Data

12/411,835, filed on Mar. 26, 2009, now Pat. No. 7,910,031, which is a continuation of application No. 12/102,071, filed on Apr. 14, 2008, now Pat. No. 7,824,588, which is a division of application No. 10/768,809, filed on Jan. 30, 2004, now Pat. No. 7,357,891, which is a continuation-in-part of application No. PCT/US12/32542, filed on Oct. 11, 2002, and a continuation-in-part of application No. PCT/US12/32575, filed on Oct. 11, 2002, and a continuation-in-part of application No. PCT/US12/32594, filed on Oct. 11, 2002, application No. 16/163,029, which is a continuation of application No. 16/155,100, filed on Oct. 9, 2018, which is a continuation of application No. 15/369,101, filed on Dec. 5, 2016, now abandoned, which is a continuation of application No. 14/196,082, filed on Mar. 4, 2014, now Pat. No. 9,511,033, which is a continuation of application No. 13/842,543, filed on Mar. 15, 2013, now abandoned, application No. 16/163,029, which is a continuation-in-part of application No. 15/699,760, filed on Sep. 8, 2017, which is a continuation of application No. 15/069,875, filed on Mar. 14, 2016, now Pat. No. 10,034,833, which is a continuation of application No. 14/814,461, filed on Jul. 30, 2015, now abandoned, which is a continuation of application No. 12/537,580, filed on Aug. 7, 2009, now abandoned.

(60) Provisional application No. 60/443,741, filed on Jan. 30, 2003, provisional application No. 60/371,940, filed on Apr. 11, 2002, provisional application No. 60/386,937, filed on Jun. 7, 2002, provisional application No. 60/328,868, filed on Oct. 12, 2001, provisional application No. 60/414,276, filed on Sep. 27, 2002.

(51) Int. Cl.
*B29C 48/91* (2019.01)
*B29C 48/88* (2019.01)

(56) References Cited

U.S. PATENT DOCUMENTS

| | | |
|---|---|---|
| 476,085 A | 5/1892 | Smith |
| 492,417 A | 2/1893 | McAlister |
| 503,070 A | 8/1893 | Broadwell et al. |
| 596,302 A | 12/1897 | McMahon |
| 688,446 A | 10/1901 | Stempel, Jr. |
| 1,110,546 A | 9/1914 | Hewitt |
| 1,827,354 A | 10/1931 | Cooper |
| 2,142,537 A | 1/1939 | Tiaxa |
| 2,277,038 A | 3/1942 | Curtis |
| 2,352,691 A | 7/1944 | Curtis |
| 2,376,656 A | 5/1945 | Leonia |
| 2,501,544 A | 3/1950 | Shrontz |
| 2,612,165 A | 9/1952 | Szukerski |
| 2,980,554 A | 4/1961 | Gentile et al. |
| 3,007,848 A | 11/1961 | Stoop |
| 3,044,338 A | 7/1962 | Horton et al. |
| 3,131,068 A | 4/1964 | Grief |
| 3,142,217 A | 7/1964 | Busse |
| 3,189,174 A | 6/1965 | Cormack |
| 3,237,596 A | 3/1966 | Grass, Jr. et al. |
| 3,242,959 A | 3/1966 | Glass |
| 3,249,109 A | 5/1966 | Maeth et al. |
| 3,324,754 A | 6/1967 | Peavy |
| 3,370,497 A | 2/1968 | Busse |
| 3,419,137 A | 12/1968 | Walck, III |
| 3,444,858 A | 5/1969 | Russell |
| 3,451,539 A | 6/1969 | Wysocki |
| 3,536,809 A | 10/1970 | Applezwig |
| 3,539,605 A | 11/1970 | Oberhofer |
| 3,551,556 A | 12/1970 | Kliment et al. |
| 3,598,122 A | 8/1971 | Zaffaroni |
| 3,610,248 A | 10/1971 | Davidson |
| 3,625,351 A | 12/1971 | Eisenberg |
| 3,632,740 A | 1/1972 | Robinson et al. |
| 3,640,741 A | 2/1972 | Etes |
| 3,641,237 A | 2/1972 | Gould et al. |
| 3,650,461 A | 3/1972 | Hutcheson |
| 3,677,866 A | 7/1972 | Pickett et al. |
| 3,731,683 A | 5/1973 | Zaffaroni |
| 3,753,732 A | 8/1973 | Boroshok |
| 3,755,558 A | 8/1973 | Scribner |
| 3,768,725 A | 10/1973 | Pilaro |
| 3,795,527 A | 3/1974 | Stone et al. |
| 3,797,494 A | 3/1974 | Zaffroni |
| 3,809,220 A | 5/1974 | Arcudi |
| 3,814,095 A | 6/1974 | Lubens |
| 3,825,014 A | 7/1974 | Wroten |
| 3,835,995 A | 9/1974 | Haines |
| 3,840,657 A | 10/1974 | Norfleet |
| 3,892,905 A | 7/1975 | Albert |
| 3,911,099 A | 10/1975 | DeFoney et al. |
| 3,933,245 A | 1/1976 | Mullen |
| 3,972,995 A | 8/1976 | Tsuk et al. |
| 3,979,839 A | 9/1976 | Blanie |
| 3,996,934 A | 12/1976 | Zaffaroni |
| 3,998,215 A | 12/1976 | Anderson et al. |
| 4,015,023 A | 3/1977 | Lamberti et al. |
| 4,022,924 A | 5/1977 | Mitchell et al. |
| 4,029,757 A | 6/1977 | Mlodozeniec et al. |
| 4,029,758 A | 6/1977 | Mlodozeniec et al. |
| 4,031,200 A | 6/1977 | Reif |
| 4,049,848 A | 9/1977 | Goodale et al. |
| 4,053,046 A | 10/1977 | Roark |
| 4,067,116 A | 1/1978 | Bryner et al. |
| 4,105,116 A | 8/1978 | Jones et al. |
| 4,123,592 A | 10/1978 | Rainer et al. |
| 4,126,503 A | 11/1978 | Gardner |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,202,966 A | 5/1980 | Misaki et al. |
| 4,226,848 A | 10/1980 | Nagai et al. |
| 4,249,531 A | 2/1981 | Heller et al. |
| 4,251,400 A | 2/1981 | Columbus |
| 4,251,561 A | 2/1981 | Gajewski |
| 4,284,194 A | 8/1981 | Flatau |
| 4,284,534 A | 8/1981 | Ehrlich |
| 4,292,299 A | 9/1981 | Suzuki et al. |
| 4,294,820 A | 10/1981 | Keith et al. |
| 4,302,465 A | 11/1981 | Ekenstam et al. |
| 4,307,075 A | 12/1981 | Martin |
| 4,307,117 A | 12/1981 | Leshik |
| 4,325,855 A | 4/1982 | Dickmann et al. |
| 4,341,563 A | 7/1982 | Kurihara et al. |
| 4,365,423 A | 12/1982 | Arter et al. |
| 4,373,036 A | 2/1983 | Chang et al. |
| 4,390,450 A | 6/1983 | Gibson et al. |
| 4,406,708 A | 9/1983 | Hesselgren |
| 4,432,975 A | 2/1984 | Libby |
| 4,438,258 A | 3/1984 | Graham |
| 4,451,260 A | 5/1984 | Mitra |
| 4,460,532 A | 7/1984 | Cornell |
| 4,460,562 A | 7/1984 | Keith et al. |
| 4,466,973 A | 8/1984 | Rennie |
| 4,478,658 A | 10/1984 | Wittwer |
| 4,483,846 A | 11/1984 | Koide et al. |
| 4,503,070 A | 3/1985 | Eby, III |
| 4,511,592 A | 4/1985 | Percel et al. |
| 4,515,162 A | 5/1985 | Yamamoto et al. |
| 4,517,173 A | 5/1985 | Kizawa et al. |
| 4,529,301 A | 7/1985 | Rountree |
| 4,529,601 A | 7/1985 | Broberg et al. |
| 4,529,748 A | 7/1985 | Wienecke |
| 4,562,020 A | 12/1985 | Hijiya et al. |
| 4,568,535 A | 2/1986 | Loesche |

(56) References Cited

U.S. PATENT DOCUMENTS

| | | |
|---|---|---|
| 4,569,837 A | 2/1986 | Suzuki et al. |
| 4,572,832 A | 2/1986 | Kigasawa et al. |
| 4,582,835 A | 4/1986 | Lewis et al. |
| 4,585,452 A | 4/1986 | Sablotsky |
| 4,588,592 A | 5/1986 | Elias |
| 4,593,053 A | 6/1986 | Jevne et al. |
| 4,598,089 A | 7/1986 | Hadvary et al. |
| 4,608,249 A | 8/1986 | Otsuka et al. |
| 4,613,497 A | 9/1986 | Chavkin |
| 4,615,697 A | 10/1986 | Robinson |
| 4,619,701 A | 10/1986 | Angrick et al. |
| 4,621,482 A | 11/1986 | Crevasse et al. |
| 4,623,394 A | 11/1986 | Nakamura et al. |
| 4,631,837 A | 12/1986 | Magoon |
| 4,639,367 A | 1/1987 | Mackles |
| 4,648,509 A | 3/1987 | Alves |
| 4,659,714 A | 4/1987 | Watt-Smith |
| 4,661,359 A | 4/1987 | Seaborne et al. |
| 4,675,009 A | 6/1987 | Hymes et al. |
| 4,695,465 A | 9/1987 | Kigasawa et al. |
| 4,704,119 A | 11/1987 | Shaw et al. |
| 4,705,174 A | 11/1987 | Goglio |
| 4,712,460 A | 12/1987 | Allen et al. |
| 4,713,239 A | 12/1987 | Babaian et al. |
| 4,713,243 A | 12/1987 | Schiraldi et al. |
| 4,713,251 A | 12/1987 | Seighman |
| 4,716,802 A | 1/1988 | O'Connor et al. |
| 4,722,761 A | 2/1988 | Cartmell et al. |
| 4,727,064 A | 2/1988 | Pitha |
| 4,740,365 A | 4/1988 | Yukimatsu et al. |
| 4,748,022 A | 5/1988 | Busciglio |
| 4,752,465 A | 6/1988 | Mackles |
| 4,762,230 A | 8/1988 | Croce |
| 4,764,378 A | 8/1988 | Keith et al. |
| 4,765,983 A | 8/1988 | Takayanagi et al. |
| 4,772,470 A | 9/1988 | Inoue et al. |
| 4,777,046 A | 10/1988 | Iwakura et al. |
| 4,780,309 A | 10/1988 | Geria et al. |
| 4,781,294 A | 11/1988 | Croce |
| 4,787,517 A | 11/1988 | Martin |
| 4,789,667 A | 12/1988 | Makino et al. |
| 4,802,924 A | 2/1989 | Woznicki et al. |
| 4,828,841 A | 5/1989 | Porter et al. |
| 4,849,246 A | 7/1989 | Schmidt |
| 4,851,394 A | 7/1989 | Kubodera |
| 4,860,754 A | 8/1989 | Sharik et al. |
| 4,861,632 A | 8/1989 | Caggiano |
| RE33,093 E | 10/1989 | Schiraldi et al. |
| 4,872,270 A | 10/1989 | Fronheiser et al. |
| 4,876,092 A | 10/1989 | Mizobuchi et al. |
| 4,876,970 A | 10/1989 | Bolduc |
| 4,880,416 A | 11/1989 | Horiuchi et al. |
| 4,888,354 A | 12/1989 | Chang et al. |
| 4,894,232 A | 1/1990 | Reul et al. |
| 4,900,552 A | 2/1990 | Sanvordeker et al. |
| 4,900,554 A | 2/1990 | Yangibashi et al. |
| 4,900,556 A | 2/1990 | Wheatley et al. |
| 4,910,247 A | 3/1990 | Haldar et al. |
| 4,915,950 A | 4/1990 | Miranda et al. |
| 4,925,670 A | 5/1990 | Schmidt |
| 4,927,634 A | 5/1990 | Sorrentino et al. |
| 4,927,636 A | 5/1990 | Hijiya et al. |
| 4,929,447 A | 5/1990 | Yang |
| 4,937,078 A | 6/1990 | Mezei et al. |
| 4,940,587 A | 7/1990 | Jenkins et al. |
| 4,948,580 A | 8/1990 | Browning |
| 4,958,580 A | 9/1990 | Asaba et al. |
| 4,978,531 A | 12/1990 | Yamazaki et al. |
| 4,980,169 A | 12/1990 | Oppenheimer et al. |
| 4,981,693 A | 1/1991 | Higashi et al. |
| 4,981,875 A | 1/1991 | Leusner et al. |
| 4,993,586 A | 2/1991 | Taulbee et al. |
| 5,023,082 A | 6/1991 | Friedman et al. |
| 5,023,271 A | 6/1991 | Vigne et al. |
| 5,024,701 A | 6/1991 | Desmarais |
| 5,025,692 A | 6/1991 | Reynolds |
| 5,028,632 A | 7/1991 | Fuisz |
| 5,044,241 A | 9/1991 | Labrecque |
| 5,044,761 A | 9/1991 | Yuhki et al. |
| 5,045,445 A | 9/1991 | Schultz |
| 5,047,244 A | 9/1991 | Sanvordeker et al. |
| 5,049,322 A | 9/1991 | Devissaguet et al. |
| 5,056,584 A | 10/1991 | Seaton |
| 5,064,717 A | 11/1991 | Suzuki et al. |
| 5,072,842 A | 12/1991 | White |
| 5,078,734 A | 1/1992 | Noble |
| 5,089,307 A | 2/1992 | Ninomiya et al. |
| 5,100,591 A | 3/1992 | Leclef et al. |
| 5,107,734 A | 4/1992 | Armbruster |
| 5,116,140 A | 5/1992 | Hirashima |
| 5,118,508 A | 6/1992 | Kikuchi et al. |
| 5,126,160 A | 6/1992 | Giddey et al. |
| 5,137,729 A | 8/1992 | Kuroya et al. |
| 5,158,825 A | 10/1992 | Altwirth |
| 5,166,233 A | 11/1992 | Kuroya et al. |
| 5,176,705 A | 1/1993 | Noble |
| 5,184,771 A | 2/1993 | Jud et al. |
| 5,186,938 A | 2/1993 | Sablotsky et al. |
| 5,188,838 A | 2/1993 | Deleuil et al. |
| 5,196,436 A | 3/1993 | Smith |
| 5,229,164 A | 7/1993 | Pins et al. |
| 5,230,441 A | 7/1993 | Kaufman et al. |
| 5,234,957 A | 8/1993 | Mantelle |
| 5,264,024 A | 11/1993 | Bosvot et al. |
| 5,271,940 A | 12/1993 | Cleary et al. |
| 5,272,191 A | 12/1993 | Ibrahim et al. |
| 5,273,758 A | 12/1993 | Royce |
| 5,293,699 A | 3/1994 | Faust et al. |
| 5,316,717 A | 5/1994 | Koepff et al. |
| 5,325,968 A | 7/1994 | Sowden |
| 5,328,942 A | 7/1994 | Akhtar et al. |
| 5,344,676 A | 9/1994 | Kim et al. |
| 5,346,701 A | 9/1994 | Heiber et al. |
| 5,354,551 A | 10/1994 | Schmidt |
| 5,360,629 A | 11/1994 | Milbourn et al. |
| 5,369,131 A | 11/1994 | Poli et al. |
| 5,375,930 A | 12/1994 | Tani |
| 5,380,529 A | 1/1995 | Heusser et al. |
| 5,393,528 A | 2/1995 | Staab |
| 5,405,637 A | 4/1995 | Martinez et al. |
| 5,407,278 A | 4/1995 | Beer |
| 5,411,945 A | 5/1995 | Ozaki et al. |
| 5,413,792 A | 5/1995 | Ninomiya et al. |
| 5,422,127 A | 6/1995 | Dube et al. |
| 5,423,423 A | 6/1995 | Sato et al. |
| 5,433,960 A | 7/1995 | Meyers |
| 5,451,419 A | 9/1995 | Schwab et al. |
| 5,455,043 A | 10/1995 | Fischel-Ghodsian |
| 5,458,884 A | 10/1995 | Britton et al. |
| 5,462,749 A | 10/1995 | Rencher |
| 5,472,704 A | 12/1995 | Santus et al. |
| 5,479,408 A | 12/1995 | Will |
| 5,489,436 A | 2/1996 | Hoy et al. |
| 5,506,046 A | 4/1996 | Andersen et al. |
| 5,506,049 A | 4/1996 | Swei et al. |
| 5,518,902 A | 5/1996 | Ozaki et al. |
| 5,529,782 A | 6/1996 | Staab |
| 5,530,861 A | 6/1996 | Diamant et al. |
| 5,550,178 A | 8/1996 | Desai et al. |
| 5,551,033 A | 8/1996 | Foster et al. |
| 5,552,152 A | 9/1996 | Shen |
| 5,553,835 A | 9/1996 | Dresie et al. |
| 5,560,538 A | 10/1996 | Sato et al. |
| 5,567,237 A | 10/1996 | Kapp-Schwoerer et al. |
| 5,567,431 A | 10/1996 | Vert et al. |
| 5,573,783 A | 11/1996 | Desieno et al. |
| 5,582,342 A | 12/1996 | Jud |
| 5,587,175 A | 12/1996 | Viegas et al. |
| 5,588,009 A | 12/1996 | Will |
| 5,589,357 A | 12/1996 | Martinez et al. |
| 5,593,697 A | 1/1997 | Barr et al. |
| 5,595,980 A | 1/1997 | Brode et al. |
| 5,601,605 A | 2/1997 | Crowe et al. |
| 5,605,696 A | 2/1997 | Eury et al. |

(56) References Cited

U.S. PATENT DOCUMENTS

| | | |
|---|---|---|
| 5,605,698 A | 2/1997 | Ueno |
| 5,613,779 A | 3/1997 | Niwa |
| 5,614,212 A | 3/1997 | D'Angelo et al. |
| 5,620,757 A | 4/1997 | Ninomiya et al. |
| 5,629,003 A | 5/1997 | Horstmann et al. |
| 5,629,021 A | 5/1997 | Wright |
| 5,633,006 A | 5/1997 | Catania et al. |
| 5,641,093 A | 6/1997 | Dolin et al. |
| 5,641,536 A | 6/1997 | Lech et al. |
| D380,836 S | 7/1997 | Fitzpatrick et al. |
| 5,647,431 A | 7/1997 | Takeshita et al. |
| 5,653,993 A | 8/1997 | Ghanta et al. |
| 5,656,296 A | 8/1997 | Khan et al. |
| 5,656,297 A | 8/1997 | Bernstein et al. |
| 5,670,168 A | 9/1997 | Baichwal et al. |
| 5,679,145 A | 10/1997 | Andersen et al. |
| 5,681,873 A | 10/1997 | Norton et al. |
| 5,689,550 A | 11/1997 | Garson et al. |
| 5,698,181 A | 12/1997 | Luo |
| 5,698,217 A | 12/1997 | Wilking |
| 5,700,478 A | 12/1997 | Biegajski et al. |
| 5,700,479 A | 12/1997 | Lundgren |
| 5,725,648 A | 3/1998 | Brown et al. |
| 5,733,575 A | 3/1998 | Mehra et al. |
| 5,738,211 A | 4/1998 | Ichino et al. |
| 5,742,905 A | 4/1998 | Pepe et al. |
| 5,750,145 A | 5/1998 | Patell |
| 5,750,157 A | 5/1998 | Grosswald et al. |
| 5,750,585 A | 5/1998 | Park et al. |
| 5,759,599 A | 6/1998 | Wampler et al. |
| 5,761,525 A | 6/1998 | Williams |
| 5,764,639 A | 6/1998 | Staples et al. |
| 5,764,899 A | 6/1998 | Eggleston et al. |
| 5,765,004 A | 6/1998 | Foster et al. |
| 5,766,332 A | 6/1998 | Graves et al. |
| 5,766,525 A | 6/1998 | Andersen et al. |
| 5,766,620 A | 6/1998 | Heiber et al. |
| 5,766,839 A | 6/1998 | Johnson et al. |
| 5,771,353 A | 6/1998 | Eggleston et al. |
| 5,785,180 A | 7/1998 | Dressel et al. |
| 5,792,494 A | 8/1998 | Kanca et al. |
| 5,800,832 A | 9/1998 | Tapolsky et al. |
| 5,806,284 A | 9/1998 | Gifford |
| 5,815,398 A | 9/1998 | Dighe et al. |
| 5,822,526 A | 10/1998 | Waskiewicz |
| 5,830,437 A | 11/1998 | Ascione et al. |
| 5,830,884 A | 11/1998 | Kasica et al. |
| 5,846,557 A | 12/1998 | Eisenstadt et al. |
| 5,847,023 A | 12/1998 | Viegas et al. |
| 5,862,915 A | 1/1999 | Plezia et al. |
| 5,864,684 A | 1/1999 | Nielsen |
| 5,881,476 A | 3/1999 | Strobush et al. |
| 5,891,461 A | 4/1999 | Jona et al. |
| 5,891,845 A | 4/1999 | Myers |
| 5,894,930 A | 4/1999 | Faughey et al. |
| 5,900,247 A | 5/1999 | Rault et al. |
| 5,906,742 A | 5/1999 | Wang et al. |
| 5,930,914 A | 8/1999 | Johansson et al. |
| 5,937,161 A | 8/1999 | Mulligan et al. |
| 5,941,393 A | 8/1999 | Wilfong, Jr. |
| 5,945,651 A | 8/1999 | Chorosinski et al. |
| 5,948,430 A | 9/1999 | Zerbe et al. |
| 5,955,097 A | 9/1999 | Tapolsky et al. |
| 5,965,154 A | 10/1999 | Haralambopoulos |
| 5,980,554 A | 11/1999 | Lenker et al. |
| 5,992,742 A | 11/1999 | Sullivan et al. |
| 5,995,597 A | 11/1999 | Woltz et al. |
| 6,004,996 A | 12/1999 | Shah et al. |
| 6,024,975 A | 2/2000 | D'Angelo et al. |
| 6,030,616 A | 2/2000 | Waters et al. |
| 6,031,895 A | 2/2000 | Cohn et al. |
| 6,036,016 A | 3/2000 | Arnold |
| 6,047,484 A | 4/2000 | Bolland et al. |
| 6,051,253 A | 4/2000 | Zettler et al. |
| 6,054,119 A | 4/2000 | Hurme et al. |
| 6,064,990 A | 5/2000 | Goldsmith |
| 6,072,100 A | 6/2000 | Mooney et al. |
| 6,074,097 A | 6/2000 | Hayashi et al. |
| 6,077,558 A | 6/2000 | Euber |
| 6,090,401 A | 7/2000 | Gowan, Jr. et al. |
| 6,099,871 A | 8/2000 | Martinez |
| 6,103,266 A | 8/2000 | Tapolsky et al. |
| 6,106,930 A | 8/2000 | Ludwig |
| 6,143,276 A | 11/2000 | Unger |
| 6,148,708 A | 11/2000 | Pfeiffer |
| 6,152,007 A | 11/2000 | Sato |
| 6,153,210 A | 11/2000 | Roberts et al. |
| 6,153,220 A | 11/2000 | Cumming et al. |
| 6,159,498 A | 12/2000 | Tapolsky et al. |
| 6,161,129 A | 12/2000 | Rochkind |
| 6,177,066 B1 | 1/2001 | Pataut et al. |
| 6,177,092 B1 | 1/2001 | Lentini et al. |
| 6,177,096 B1 | 1/2001 | Zerbe et al. |
| 6,183,808 B1 | 2/2001 | Grillo et al. |
| 6,197,329 B1 | 3/2001 | Hermelin et al. |
| 6,203,566 B1 | 3/2001 | Alanen et al. |
| 6,219,694 B1 | 4/2001 | Lazaridis et al. |
| 6,221,402 B1 | 4/2001 | Itoh et al. |
| 6,227,359 B1 | 5/2001 | Truluck |
| 6,230,894 B1 | 5/2001 | Danville |
| 6,231,957 B1 | 5/2001 | Zerbe et al. |
| 6,238,700 B1 | 5/2001 | Dohner et al. |
| 6,264,981 B1 | 7/2001 | Zhang et al. |
| 6,267,808 B1 | 7/2001 | Grillo et al. |
| 6,268,048 B1 | 7/2001 | Topolkaraev et al. |
| 6,284,264 B1 | 9/2001 | Zerbe et al. |
| 6,287,595 B1 | 9/2001 | Loewy et al. |
| 6,294,206 B1 | 9/2001 | Barrett-Reis et al. |
| 6,311,627 B1 | 11/2001 | Draper et al. |
| 6,338,407 B2 | 1/2002 | Danville |
| 6,344,088 B1 | 2/2002 | Kamikihara et al. |
| 6,374,715 B1 | 4/2002 | Takatsuka |
| 6,375,963 B1 | 4/2002 | Repka et al. |
| 6,391,294 B1 | 5/2002 | Dettmar et al. |
| 6,394,306 B1 | 5/2002 | Pawlo et al. |
| 6,395,299 B1 | 5/2002 | Babich et al. |
| 6,413,792 B1 | 7/2002 | Sauer et al. |
| 6,419,903 B1 | 7/2002 | Xu et al. |
| 6,419,906 B1 | 7/2002 | Xu et al. |
| 6,428,825 B2 | 8/2002 | Sharma et al. |
| 6,432,460 B1 | 8/2002 | Zietlow et al. |
| 6,436,464 B1 | 8/2002 | Euber |
| 6,454,788 B1 | 9/2002 | Ashton |
| 6,467,621 B1 | 10/2002 | Ishida |
| 6,468,516 B1 | 10/2002 | Geria et al. |
| 6,472,003 B2 | 10/2002 | Barrett-Reis et al. |
| 6,482,517 B1 | 11/2002 | Anderson |
| 6,488,963 B1 | 12/2002 | McGinity et al. |
| 6,495,599 B2 | 12/2002 | Auestad et al. |
| 6,503,532 B1 | 1/2003 | Murty et al. |
| 6,509,072 B2 | 1/2003 | Bening et al. |
| 6,534,090 B2 | 3/2003 | Puthli et al. |
| 6,534,092 B2 | 3/2003 | Wright |
| 6,552,024 B1 | 4/2003 | Chen et al. |
| 6,562,375 B1 | 5/2003 | Sako et al. |
| 6,575,999 B1 | 6/2003 | Rohrig |
| 6,589,576 B2 | 7/2003 | Borschel et al. |
| 6,592,887 B2 | 7/2003 | Zerbe et al. |
| 6,596,298 B2 | 7/2003 | Leung et al. |
| 6,596,302 B2 | 7/2003 | O'Connor et al. |
| 6,599,542 B1 | 7/2003 | Abdel-Malik et al. |
| 6,610,338 B2 | 8/2003 | Tang |
| 6,620,440 B1 | 9/2003 | Hsia et al. |
| 6,655,112 B1 | 12/2003 | Cremer et al. |
| 6,656,493 B2 | 12/2003 | Dzija et al. |
| 6,660,292 B2 | 12/2003 | Zerbe et al. |
| 6,667,060 B1 | 12/2003 | Vandecruys et al. |
| 6,668,839 B2 | 12/2003 | Williams |
| 6,708,826 B1 | 3/2004 | Ginsberg et al. |
| 6,709,671 B2 | 3/2004 | Zerbe et al. |
| 6,720,006 B2 | 4/2004 | Hanke et al. |
| 6,726,054 B2 | 4/2004 | Fagen et al. |
| 6,730,319 B2 | 5/2004 | Maeder et al. |
| 6,752,824 B2 | 6/2004 | Yancy |

(56) References Cited

U.S. PATENT DOCUMENTS

| | | |
|---|---|---|
| 6,776,157 B2 | 8/2004 | Williams et al. |
| 6,797,283 B1 | 9/2004 | Edgren et al. |
| 6,800,329 B2 | 10/2004 | Horstmann et al. |
| 6,824,829 B2 | 11/2004 | Berry et al. |
| 6,865,860 B2 | 3/2005 | Arakawa et al. |
| 6,905,016 B2 | 6/2005 | Kanios et al. |
| 6,913,766 B1 | 7/2005 | Krumme et al. |
| 6,929,399 B2 | 8/2005 | Nokura |
| 6,929,400 B2 | 8/2005 | Razeti et al. |
| 7,005,142 B2 | 2/2006 | Leon et al. |
| 7,040,503 B2 | 5/2006 | Leichter et al. |
| 7,067,116 B1 | 6/2006 | Bess et al. |
| 7,093,736 B2 | 8/2006 | Maietta et al. |
| 7,115,507 B2 | 10/2006 | Kawase |
| 7,179,788 B2 | 2/2007 | DeFelippis et al. |
| 7,241,411 B2 | 7/2007 | Berry et al. |
| 7,357,891 B2 | 4/2008 | Yang et al. |
| 7,390,503 B1 | 6/2008 | Ahmed et al. |
| 7,425,292 B2 | 9/2008 | Yang et al. |
| 7,428,859 B2 | 9/2008 | Fujita et al. |
| 7,484,640 B2 | 2/2009 | von Falkenhausen et al. |
| 7,531,191 B2 | 5/2009 | Zion et al. |
| 7,579,019 B2 | 8/2009 | Tapolsky et al. |
| 7,591,801 B2 | 9/2009 | Brauker et al. |
| 7,665,896 B1 | 2/2010 | Higgs |
| 7,666,337 B2 | 2/2010 | Yang et al. |
| 7,694,617 B2 | 4/2010 | Habra et al. |
| 7,824,588 B2 | 11/2010 | Yang et al. |
| 7,910,031 B2 | 3/2011 | Yang et al. |
| 8,017,150 B2 | 9/2011 | Yang et al. |
| 8,051,983 B2 | 11/2011 | Simon et al. |
| 8,147,866 B2 | 4/2012 | Finn et al. |
| 2001/0006677 A1 | 7/2001 | McGinity et al. |
| 2001/0022964 A1 | 9/2001 | Leung et al. |
| 2001/0046511 A1 | 11/2001 | Zerbe et al. |
| 2002/0006677 A1 | 1/2002 | Egermeier et al. |
| 2002/0012689 A1 | 1/2002 | Stillman |
| 2002/0045582 A1 | 4/2002 | Margolin et al. |
| 2002/0098198 A1 | 7/2002 | Watts et al. |
| 2002/0104774 A1 | 8/2002 | Hammond |
| 2002/0127254 A1 | 9/2002 | Fotinos et al. |
| 2002/0131990 A1 | 9/2002 | Barkalow et al. |
| 2002/0147201 A1 | 10/2002 | Chen et al. |
| 2002/0170567 A1 | 11/2002 | Rizzotto et al. |
| 2002/0177380 A1 | 11/2002 | Forman et al. |
| 2003/0035841 A1 | 2/2003 | Dzija et al. |
| 2003/0044511 A1 | 3/2003 | Zerbe et al. |
| 2003/0054039 A1 | 3/2003 | Zyck et al. |
| 2003/0068378 A1 | 4/2003 | Chen et al. |
| 2003/0069263 A1 | 4/2003 | Breder et al. |
| 2003/0072865 A1 | 4/2003 | Bindels et al. |
| 2003/0077315 A1 | 4/2003 | Lee et al. |
| 2003/0107149 A1 | 6/2003 | Yang et al. |
| 2003/0118649 A1 | 6/2003 | Gao et al. |
| 2003/0121932 A1 | 7/2003 | Wajda |
| 2003/0124176 A1 | 7/2003 | Hsu et al. |
| 2003/0140760 A1 | 7/2003 | Bory |
| 2003/0147956 A1 | 8/2003 | Shefer et al. |
| 2003/0161926 A1 | 8/2003 | Kemp et al. |
| 2003/0183643 A1 | 10/2003 | Fagen et al. |
| 2003/0224044 A1 | 12/2003 | Weibel |
| 2004/0013731 A1 | 1/2004 | Chen et al. |
| 2004/0024003 A1 | 2/2004 | Asmussen et al. |
| 2004/0044367 A1 | 3/2004 | Yancy |
| 2004/0058457 A1 | 3/2004 | Huang et al. |
| 2004/0091677 A1 | 5/2004 | Topolkaraev |
| 2004/0096569 A1 | 5/2004 | Barkalow et al. |
| 2004/0102867 A1 | 5/2004 | Palanisamy et al. |
| 2004/0111275 A1 | 6/2004 | Kroll et al. |
| 2004/0120991 A1 | 6/2004 | Gardner et al. |
| 2004/0136924 A1 | 7/2004 | Boyd et al. |
| 2004/0137458 A1 | 7/2004 | Archambault et al. |
| 2004/0156901 A1 | 8/2004 | Thakur et al. |
| 2004/0191302 A1 | 9/2004 | Davidson |
| 2004/0209057 A1 | 10/2004 | Enlow et al. |
| 2004/0219109 A1 | 11/2004 | Hatch |
| 2004/0241242 A1 | 12/2004 | Fuisz et al. |
| 2005/0003048 A1 | 1/2005 | Pearce et al. |
| 2005/0011776 A1 | 1/2005 | Nagel |
| 2005/0019588 A1 | 1/2005 | Berry et al. |
| 2005/0035133 A1 | 2/2005 | Gerulski et al. |
| 2005/0037055 A1 | 2/2005 | Yang et al. |
| 2005/0048102 A1 | 3/2005 | Tapolsky et al. |
| 2005/0055123 A1 | 3/2005 | Franz |
| 2005/0089548 A1 | 4/2005 | Virgalitto et al. |
| 2005/0095272 A1 | 5/2005 | Augello |
| 2005/0115862 A1 | 6/2005 | Maietta |
| 2005/0118217 A1 | 6/2005 | Barnhart et al. |
| 2005/0118271 A1 | 6/2005 | Schliecker et al. |
| 2005/0136115 A1 | 6/2005 | Kulkarni et al. |
| 2005/0147658 A1 | 7/2005 | Tapolsky et al. |
| 2005/0163714 A1 | 7/2005 | Sukhishvili et al. |
| 2005/0170138 A1 | 8/2005 | Berry |
| 2005/0191349 A1 | 9/2005 | Boehm et al. |
| 2005/0192309 A1 | 9/2005 | Palermo et al. |
| 2005/0214251 A1 | 9/2005 | Pohl et al. |
| 2005/0222781 A1 | 10/2005 | Yue et al. |
| 2005/0232977 A1 | 10/2005 | Khan et al. |
| 2005/0239845 A1 | 10/2005 | Proehl et al. |
| 2006/0023976 A1 | 2/2006 | Alvater et al. |
| 2006/0039958 A1 | 2/2006 | Fuisz et al. |
| 2006/0071057 A1 | 4/2006 | Aschenbrenner et al. |
| 2006/0073190 A1 | 4/2006 | Carroll et al. |
| 2006/0083786 A1 | 4/2006 | Chaudhari et al. |
| 2006/0093679 A1 | 5/2006 | Mayer et al. |
| 2006/0104910 A1 | 5/2006 | Lerner |
| 2006/0147493 A1 | 7/2006 | Yang et al. |
| 2006/0163269 A1 | 7/2006 | Anderson et al. |
| 2006/0180604 A1 | 8/2006 | Ginsberg et al. |
| 2006/0182796 A1 | 8/2006 | Wu et al. |
| 2006/0189772 A1 | 8/2006 | Scheibel et al. |
| 2006/0198790 A1 | 9/2006 | Dugger, III et al. |
| 2006/0198885 A1 | 9/2006 | Dharmadhikari et al. |
| 2006/0210610 A1 | 9/2006 | Davidson et al. |
| 2006/0213348 A1 | 9/2006 | Loibl |
| 2006/0215941 A1 | 9/2006 | Golbert |
| 2006/0246141 A1 | 11/2006 | Liversidge et al. |
| 2006/0264448 A1 | 11/2006 | Pryde |
| 2006/0281775 A1 | 12/2006 | Kelly, II et al. |
| 2006/0286108 A1 | 12/2006 | Bell |
| 2007/0027213 A1 | 2/2007 | Oberegger et al. |
| 2007/0045148 A1 | 3/2007 | Saclier et al. |
| 2007/0069416 A1 | 3/2007 | Yang et al. |
| 2007/0087036 A1 | 4/2007 | Durschlag et al. |
| 2007/0098746 A1 | 5/2007 | Nichols et al. |
| 2007/0122455 A1 | 5/2007 | Myers et al. |
| 2007/0138049 A1 | 6/2007 | Bitner |
| 2007/0148097 A1 | 6/2007 | Finn et al. |
| 2007/0170196 A1 | 7/2007 | Libohova et al. |
| 2007/0205127 A1 | 9/2007 | Barndt et al. |
| 2007/0231368 A1 | 10/2007 | Wang et al. |
| 2007/0267433 A1 | 11/2007 | Fuisz et al. |
| 2007/0281003 A1 | 12/2007 | Fuisz et al. |
| 2008/0044454 A1 | 2/2008 | Yang et al. |
| 2008/0073235 A1 | 3/2008 | Harada et al. |
| 2008/0075825 A1 | 3/2008 | Fuisz et al. |
| 2008/0081071 A1 | 4/2008 | Sanghvi et al. |
| 2008/0105582 A1 | 5/2008 | Ludwig et al. |
| 2008/0233174 A1 | 9/2008 | Myers et al. |
| 2008/0242558 A1 | 10/2008 | Belcher et al. |
| 2008/0242736 A1 | 10/2008 | Fuisz |
| 2008/0254105 A1 | 10/2008 | Tapolsky et al. |
| 2008/0260805 A1 | 10/2008 | Yang et al. |
| 2008/0260809 A1 | 10/2008 | Yang et al. |
| 2008/0268116 A1 | 10/2008 | Kring |
| 2008/0290106 A1 | 11/2008 | van der Klaauw et al. |
| 2008/0299197 A1 | 12/2008 | Tongeguzzo et al. |
| 2008/0300173 A1 | 12/2008 | DeFrees |
| 2008/0308449 A1 | 12/2008 | Intini |
| 2009/0004254 A1 | 1/2009 | Maibach |
| 2009/0009332 A1 | 1/2009 | Nunez et al. |
| 2009/0014491 A1 | 1/2009 | Fuisz et al. |
| 2009/0029074 A1 | 1/2009 | Sasine et al. |
| 2009/0074333 A1 | 3/2009 | Griebel et al. |

(56) References Cited

U.S. PATENT DOCUMENTS

| | | |
|---|---|---|
| 2009/0104270 A1 | 4/2009 | Myers et al. |
| 2009/0146336 A1 | 6/2009 | Masi |
| 2009/0181075 A1 | 7/2009 | Gordon et al. |
| 2009/0192075 A1 | 7/2009 | Steiner |
| 2009/0196907 A1 | 8/2009 | Bunick et al. |
| 2009/0297614 A1 | 12/2009 | Rademacher et al. |
| 2010/0015128 A1 | 1/2010 | Lee et al. |
| 2010/0087470 A1 | 4/2010 | Oksche et al. |
| 2010/0092545 A1 | 4/2010 | Yang et al. |
| 2010/0178254 A1 | 7/2010 | Hariharan et al. |
| 2010/0221309 A1 | 9/2010 | Myers et al. |
| 2010/0297232 A1 | 11/2010 | Myers et al. |
| 2011/0189259 A1 | 8/2011 | Vasisht et al. |
| 2011/0262522 A1 | 10/2011 | Finn et al. |

FOREIGN PATENT DOCUMENTS

| | | |
|---|---|---|
| CA | 2317491 C | 6/2008 |
| CH | 639619 A5 | 11/1983 |
| CN | 1118254 A | 3/1996 |
| DE | 2746414 A1 | 4/1979 |
| DE | 2449865 B2 | 6/1981 |
| DE | 2432925 C3 | 11/1985 |
| DE | 3630603 C2 | 6/1989 |
| DE | 19646392 A1 | 5/1998 |
| DE | 202004003781 U1 | 5/2004 |
| EP | 0014253 A2 | 8/1980 |
| EP | 0021178 B1 | 1/1981 |
| EP | 0090560 A2 | 10/1983 |
| EP | 0095892 A1 | 12/1983 |
| EP | 0065370 B1 | 1/1985 |
| EP | 0248548 B1 | 5/1987 |
| EP | 0232877 A2 | 8/1987 |
| EP | 0241178 | 10/1987 |
| EP | 0285568 A2 | 3/1988 |
| EP | 0274431 A2 | 7/1988 |
| EP | 0219762 B1 | 12/1990 |
| EP | 0259749 B1 | 8/1991 |
| EP | 0200508 B1 | 10/1991 |
| EP | 0241178 B1 | 1/1992 |
| EP | 0514691 A2 | 4/1992 |
| EP | 0273069 B1 | 10/1992 |
| EP | 0250187 B1 | 9/1993 |
| EP | 0452446 B1 | 12/1993 |
| EP | 0598606 A1 | 5/1994 |
| EP | 0381194 B1 | 8/1994 |
| EP | 0440462 B1 | 12/1994 |
| EP | 0636364 A1 | 1/1995 |
| EP | 0450141 B1 | 5/1995 |
| EP | 0460588 B1 | 8/1995 |
| EP | 0514691 B1 | 1/1996 |
| EP | 0598606 B1 | 6/1999 |
| EP | 1143940 | 7/2000 |
| EP | 1110546 A1 | 6/2001 |
| EP | 1177788 A2 | 2/2002 |
| EP | 1219291 A1 | 3/2002 |
| EP | 1243523 A1 | 9/2002 |
| EP | 0949925 B1 | 1/2004 |
| EP | 1504765 A1 | 2/2005 |
| EP | 1267829 B1 | 5/2006 |
| EP | 1674078 A2 | 6/2006 |
| EP | 1852041 A2 | 11/2007 |
| EP | 1897543 A1 | 3/2008 |
| EP | 1591106 B1 | 7/2009 |
| EP | 2105389 A1 | 9/2009 |
| EP | 2253224 A1 | 11/2010 |
| EP | 2305310 A1 | 4/2011 |
| FR | 2716098 A1 | 8/1995 |
| GB | 1061557 | 3/1967 |
| GB | 1154317 | 6/1969 |
| GB | 1510999 | 5/1978 |
| GB | 2166651 A | 5/1986 |
| GB | 2447016 A | 9/2009 |
| JP | 56100714 A | 8/1981 |
| JP | 62126950 A | 6/1987 |
| JP | 2265444 A | 10/1990 |
| JP | 473268 A | 3/1992 |
| JP | 5147140 A | 6/1993 |
| JP | 7322812 A | 12/1995 |
| JP | 11255247 A | 9/1999 |
| JP | 2000159658 A | 6/2000 |
| JP | 2001048196 A | 2/2001 |
| JP | 2001225851 A | 8/2001 |
| JP | 2001279100 A | 10/2001 |
| JP | 2003312688 A | 11/2003 |
| JP | 2004222663 A | 8/2004 |
| JP | 2006143335 A | 6/2006 |
| JP | 2008011194 A | 1/2008 |
| WO | 1988007103 | 9/1988 |
| WO | 9105540 A1 | 5/1991 |
| WO | 1992012704 | 8/1992 |
| WO | 9215289 A1 | 9/1992 |
| WO | 9505416 A2 | 2/1995 |
| WO | 9518046 A1 | 7/1995 |
| WO | 1995023596 | 9/1995 |
| WO | 9530601 A1 | 11/1995 |
| WO | 9615903 A1 | 5/1996 |
| WO | 9625150 A1 | 8/1996 |
| WO | 1996025638 | 8/1996 |
| WO | 9731621 A1 | 9/1997 |
| WO | 9732573 A1 | 9/1997 |
| WO | 1997044016 | 11/1997 |
| WO | 9810993 A1 | 3/1998 |
| WO | 9817251 A1 | 4/1998 |
| WO | 1998014179 | 4/1998 |
| WO | 9935051 A1 | 7/1999 |
| WO | 9955312 A2 | 11/1999 |
| WO | 200002536 | 1/2000 |
| WO | 2000002955 | 1/2000 |
| WO | 0018365 A2 | 4/2000 |
| WO | 2000/027618 A1 | 5/2000 |
| WO | 0024647 A1 | 5/2000 |
| WO | 0042992 A2 | 7/2000 |
| WO | 2000057858 | 10/2000 |
| WO | 2001003917 A2 | 1/2001 |
| WO | 0130288 A1 | 5/2001 |
| WO | 2001034121 | 5/2001 |
| WO | 0143728 A1 | 6/2001 |
| WO | 0156904 A1 | 8/2001 |
| WO | 0168452 A1 | 9/2001 |
| WO | 0170194 A1 | 9/2001 |
| WO | 0170197 A2 | 9/2001 |
| WO | 0191721 A2 | 12/2001 |
| WO | 0205789 A2 | 1/2002 |
| WO | 0207711 A1 | 1/2002 |
| WO | 2002005820 A1 | 1/2002 |
| WO | 2006017462 A2 | 2/2002 |
| WO | 0243657 A2 | 6/2002 |
| WO | 2002/064148 A2 | 8/2002 |
| WO | 02062315 A1 | 8/2002 |
| WO | 02074238 A2 | 9/2002 |
| WO | PCT/US02/32542 | 10/2002 |
| WO | PCT/US02/32575 | 10/2002 |
| WO | PCT/US02/32594 | 10/2002 |
| WO | 02091965 A1 | 11/2002 |
| WO | 03011259 A1 | 2/2003 |
| WO | 03015749 A1 | 2/2003 |
| WO | 03030881 A1 | 4/2003 |
| WO | 03030882 A1 | 4/2003 |
| WO | 03030883 A1 | 4/2003 |
| WO | 03043659 A1 | 5/2003 |
| WO | 2003/101357 | 12/2003 |
| WO | 2004009445 A2 | 1/2004 |
| WO | 2004035407 A1 | 4/2004 |
| WO | 2004043165 A1 | 5/2004 |
| WO | PCT/US04/17076 | 5/2004 |
| WO | 2004045305 A2 | 6/2004 |
| WO | 2004045537 A2 | 6/2004 |
| WO | 2004052335 A1 | 6/2004 |
| WO | 2004060298 A2 | 7/2004 |
| WO | 2004087084 A1 | 10/2004 |
| WO | 2004113193 A1 | 12/2004 |
| WO | 2005020933 A2 | 3/2005 |
| WO | 2005035776 A2 | 4/2005 |

(56) References Cited

FOREIGN PATENT DOCUMENTS

| WO | 2005039499 A2 | 5/2005 |
|---|---|---|
| WO | 2005074867 A1 | 8/2005 |
| WO | 2005102287 A2 | 11/2005 |
| WO | 2005102863 A1 | 11/2005 |
| WO | 2005123074 A1 | 12/2005 |
| WO | 2006004480 A1 | 1/2006 |
| WO | 2006031209 A1 | 3/2006 |
| WO | 2006037979 A2 | 4/2006 |
| WO | 2006039264 A1 | 4/2006 |
| WO | 2006037425 A1 | 8/2006 |
| WO | 2006085210 A1 | 8/2006 |
| WO | 2006133948 A2 | 12/2006 |
| WO | 2007015105 A2 | 2/2007 |
| WO | 2007067494 A1 | 6/2007 |
| WO | 2007070632 A2 | 6/2007 |
| WO | PCT/US07/79357 | 9/2007 |
| WO | 2008011194 A2 | 1/2008 |
| WO | 2008025791 A1 | 3/2008 |
| WO | 2008036299 A2 | 3/2008 |
| WO | 2008040534 A2 | 4/2008 |
| WO | 2009044118 A2 | 4/2009 |
| WO | 2009052421 A1 | 4/2009 |
| WO | 2009027625 A2 | 5/2009 |
| WO | 2009105540 A1 | 8/2009 |
| WO | PCT/US11/36244 | 5/2011 |

OTHER PUBLICATIONS

CAS Presents, "Common Chemistry", http://www.commonchemistry.org.ChemicalDetail.aspx?ref=25322-68-3&terms=polyeth . . . Oct. 28, 2009.
Huus et al., "Thermal Dissociation and Unfolding of Insulin", Biochemistry, 44: 11171-11177 (2005).
Steiner et al., "Organic Derivatives of Alginic Acid", Industrial and Engineering Chemistry; 43(9): 2073-2077 (1951).
Verdampfung, Kristallisation, Trocknung (Gnielinski, V. et al., (Eds.)), pp. 161-181 (Vieweg & Sohn Verlagsgsellschaft mbH 1993). (partial English translation included.).
Giunchedi, R and Conte, U., "Spray-drying as a preparation method of microparticulate drug delivery systems : an overview," S.T.P. Pharma. Sciences 6(4):276-290 (1995).
Guo, J.H. and Zerbe, H., "Water Soluble Film for Oral Administration," The 24th International Symposium on Controlled Release of Bioactive Materials, pp. 227-229 (Paper No. 5001-5003) (1997).
The Theory and Practice of Industrial Pharmacy (3rd Ed.) (Lachman, L et al. (eds.)), pp. 47-48, 51, 57, 64, 123-127, 346-369, 453-454, 461, 470, 479, 484, 491-492, 654-655 (1986).
Physical Pharmacy (4th Ed.) (Martin, A. et al. (eds.)), pp. 423, 430-434, 453, 461, 484, 557-558, 560, 565-567 (1993).
Bioadhesive Drug Delivery Systems (Lenaerts, V. and Gurny, R. (eds.)), Ch. 6, pp. 106-136 (1990).
Introductory Polymer Chemistry (Misra, G.S. (ed.)), Ch. 6, pp. 98-118 (1993).
Nishaoka, Y. et al., "Laser Diffraction Estimation of Particle Size Distribution of Slightly Water-Soluble Drugs Coexisting with Additives: Application to Solid Dosage Forms," Chem. Pharm. Bull. 40(6):1563-1568 (1992).
Perumal, V.A. and Govender, T., "Investigating a New Approach to Film Casting for Enhanced Drug Content Uniformity in Polymeric Films," Drug Development and Industrial Pharmacy, 34:1034-1047 (2008).
Remington's Pharmaceutical Sciences (17th Ed.) (Gennaro, A.R. (ed.)), Ch. 37, pp. 713-740 (1985).
Shu, X.Z., et al., "Novel pH-sensitive citrate cross-linked chitosan film drug controlled release," Int. J. Pharmaceutics 212:19-28 (2001).
"Cellulose" Kirk-Othmer Concise Encyclopeida of Chemical Technology; Abridged version of the 24 Volume, NY, Wiley; 227-228 (1978-1984).

"Excipients, Croscarmellose Sodium", Pformulate Excipients, http://www.pformulate.com/croscarmellose.htm (Sep. 29, 2002).
Atridox(R) (Doxycycline Hyclate) Product Label.
Barton, S. et al "Citric Buffer Calculation", Version 1.1, Nov. 19, 2000.
Birkhauser, "Cell Encapsulation Technology and Therapeutics" (Jan. 5, 2009).
Bodmeier, Roland, "Evaluation of Drug-Containing Polymer Films Prepared from Aqueous Latexes", Pharmaceutical Research, vol. 6, No. 8 (1989).
Cholewinski et al., Pharmaceutica Acta Helvetiae, 71:405-419, 1996.
Croscarmellose sodium http://ww.nbent.com/crosscarmellose.htm (Mar. 29, 2005).
Delsym Product Label (Feb. 13, 2007).
Di Donato et al., J. Biol. Chem, 268(7): 4745-4751, 1993.
Eiamtrakarn et al., "Gastrointestinal Mucoadhesive Path System (GI-MAPS) for oral administration of G-CSF, a model protein", Bipmaterials 23: 145-152 (2002).
Endo and Ueda, Fabad J. Pharm. Sci., 29:27-38, 2004.
Engel, June V PhD, "The Benefits of Eating Fibre" http://www.diabetes.ca/common/PrintVersion.asp?ID=45493 May 11, 2005.
Flick, E., Water-Soluble Resins—An Industrial Guide, 1991 (2nd Ed.) William Andrew Publishing/Noyes, pp. 389-392.
Goldberg et al., "Biotechnology and Food Ingredients", Springer: 352 (1991).
Hadvary et al., "Inhibition of pancreatic lipase in vitro by the covalent inhibitor tetrahydrolistatin", Biochem J.; 256: 357-361 (1988).
Ko et al., "Behavior of etrahydrolipstatin in biological model membranes and emulsions", J. of Lipid Research; 38:1544-1552 (1997).
Kuhtreiber. In Cell Encapsulation and Therapeutics . Copyright 1999.
Lazaridou et al.; Thermophysical properties of chitosan, chitosanstarch and chitosan-pullulan films near the glass transition; Elsevier Science Ltd.; 2002; pp. 179-190.
Leathers, Appl. Microbiol. Biotechnol., 62: 468-473, 2003.
Le Person, S. Le et al., "Near infrared drying of pharmaceutical thin films: experimental analysis of internal mass transport," Chemical Engineering and Processing; (1998) pp. 257-263, 37.
Mahmood et al., "A limited sampling method for the estimation of AUC and Cmax of cabamazepine and carbamazepine epoxide folowing a single and multiple dose of a sustained-release product", BR J Clin Pharmacol; 45:241-246 (1998).
Mix. http://www.askoxford.com/concise_oed/mixx?view=uk. Accessed Dec. 23, 2004.
Nicorete Packaging (Aug. 29, 2006).
Oriski, S.C., "Johnson debuts cutter for new Saran film" Packaging World Oct. 1, 2004, http://www.packworld.com/view-18051.
Peh Kok Khiang et al., "Polymeric Films as Vehicle for Buccal Delivery: Swelling, Mechanical, and Bioadhesive Properties," J Pharm Pharmaceut Sci (1999) pp. 53-61, 2:2.
Polyethylenglykoke, Fachgebit Chemie, Unterthema Makromolekulare Chemie, XP-002298105 (Sep. 20, 2004).
Repka et al., "Bioadhesive properties of hydroxypropylcellulose topical films produced by hot-melt extrusion," Journal of Controlled Release, 70: 341-351 (2001).
Repka et al., "Influence of Vitamin E TPGS on the properties of hydrophilic films produced by hot-melt extrusion," Int. J. Pharmaceutics, 202: 63-70 (2000).
Senel, S., et al., "Chitosan films and hydrogels of chlorhexidine gluconate for oral mucosal delivery", Int. J. Pharmaceutics, 193: pp. 197-203 (2000).
Stella, V., et al., "Gliadin Films. I: Preparation and in vitro evaluation as a carrier for controlled drug release", Int., J. Pharmaceutics, 121: pp. 117-121 (1995).
Sudafed & Sudafed PE, http://www.sudafed.com/products/pe_quickstrips.html (Aug. 17, 2007).
Well—Definition of from The American Heritage College Dictionary, 3rd Ed., p. 1531 (1993).
Bauer, K.H. et al., "Pharmazeutische Technologie", pp. 208-209 (1997).

(56) References Cited

OTHER PUBLICATIONS

Pinnamanemi, S. et al., "Formulation approaches for orally administered poorly soluble drugs", Pharmazie 57(5): 291-300 (2002).
Chaumeil, J.C., "Micronization: A Method of Improving the Bioavailability of Poorly Soluble Drugs", Methods and Findings in Experimental and Clinical Pharmacology 20(3): 211-215 (1998).
Voigt, R. et al., "Pharmaseutische Technology fur Studium und Berf", pp. 179-180 (1995).
Nanda, A. et al., "An update on taste masking technologies for oral pharmaceuticals", Indian J Pharma Sci 64(1): 10-17 (2002).
Bornschein, M. et al., "Micro- und Nanopartikeln als Arzneliestofftragersysteme unter besonderer Berucksichtigung der Herstellungsmethoden", Die Pharmazie 44(9): 585-593 (1989).
Cohen E. et al., "Modern Coating and Drying Technology", pp. 268-277 (1992).
Transaction History for Ex Parte Reexamination Control No. 90/012,098, current as of Aug. 29, 2017.
Index of Documents for Inter Partes Review Case No. IPR2013-00316, current as of Aug. 29, 2017.
Transaction History for Ex Parte Reexamination Control No. 90/012,097, current as of Aug. 29, 2017.
Index of Documents for Inter Partes Review Case No. IPR2013-00315, current as of Aug. 29, 2017.
Transaction History for Inter Partes Reexamination Control No. 95/002,171, current as of Aug. 29, 2017.
Transaction History for Inter Partes Reexamination Control No. 95/001,753, current as of Aug. 29, 2017.
Transaction History for Inter Partes Reexamination Control No. 95/002,170, current as of Aug. 29, 2017.
Index of Documents for Inter Partes Review Case No. IPR2014-00794, current as of Aug. 29, 2017.
Index of Documents for Inter Partes Review Case No. IPR2015-00165, current as of Aug. 29, 2017.
Index of Documents for Inter Partes Review Case No. IPR2015-00167, current as of Aug. 29, 2017.
Index of Documents for Inter Partes Review Case No. IPR2015-00168, current as of Aug. 29, 2017.
Index of Documents for Inter Partes Review Case No. IPR2015-00169, current as of Aug. 29, 2017.
Index of Documents for Inter Partes Review Case No. IPR2016-00281, current as of Aug. 29, 2017.
Index of Documents for Inter Partes Review Case No. IPR2016-00282, current as of Aug. 29, 2017.
Index of Documents for Inter Partes Review Case No. IPR2016-01111, current as of Aug. 29, 2017.
Index of Documents for Inter Partes Review Case No. IPR2016-01112, current as of Aug. 29, 2017.
Index of Documents for Inter Partes Review Case No. IPR2017-00200, current as of Aug. 29, 2017.
Index of Documents for Inter Partes Review Case No. IPR2017-01557, current as of Aug. 29, 2017.
Index of Documents for Inter Partes Review Case No. IPR2017-01582, current as of Aug. 29, 2017.
Al-Ghananeem et al., "Effect of pH on Sublingual Absorption of Oxycodone Hydrochloride", AAPS PharmSciTech; Article 23, 7(1) (2006) (http://www.aapspharmscitec.org).
Bhumkar et al., "Chitosan Reduced Gold Nanoparticles as Novel Carriers for Transmucosal Delivery of Insulin", Pharmaceutical Research; 24(8): 1415-1426 (2007).
Bowen P., "Particle Size Distribution Measurement from Millimeters to Nanometers and from Rods to Platelets", Journal of Dispersion Science and Technology; 23(5): 631-662 (2002).
Trademark Reg. No. 2,944,841—registered Apr. 26, 2005 to Reynolds Metal Co for "EZ Slide".
Hariharan et al., "Thin Film Technology, Orally Dissolving Film Strips (ODFS): The Final Evolution of Orally Dissolving Dosage Forms," Drug Delivery Technology; 9(2): 24-29 (2009).
Joshi et al., "Gold Nanoparticles as Carrier for Efficient Transmucosal Insulin Delivery", Langmuir; 22: 300-305 (2006).
Ojeda et al., "Preparation of multifunctional glyconanoparticles as a platform for potential carbohydrate-based anticancer vaccines", Carbohydrate Research; 342: 448-459 (2007).
U.S. Department of Health and Human Services Food and Drug Administration Center for Drug Evaluation and Research (CDER) "Guidance for Industry—Incorporation of Physical-Chemical Identifiers into Solid Oral Dosage Form Drug Products for Anticounterfeiting" Silver Spring, MD; 1-8 (Jul. 9, 2009).
Boo, Woong Jae, "Characterization of Thin Film Properties of Melamine Based Dendrimer Nanoparticles", Thesis for Texas A&M University, Dec. 2003.
"Suboxone Subligualtabletten" in: Verlag Rote Liste Service GmbH: "Rote Liste 2008" 2008, Verlag Rote Liste Service GmbH, Frankfurt/Main, XP00264986, p. 39018, the whole document.
"Adsorption at Solid Surfaces," Encyclopedia of Pharmaceutical Technology (Swarbrick (ed.)), pp. 73 (1988).
Photograph of Tetracycline HCL (https://de.wikipedia.org/wiki/Tetracycline#/media/File:Tetracycline-HCL_substance_photo.jpg).
Textbook of Polymer Science (2nd Ed.) pp. 1-22 (Wiley 1971).
Thimmashetty, J. et al, "Preparation and Evaluation of Buccal Dosage Forms of Insulin."
Thimmashetty, J. et al, "Design and In Vivo Evaluation of Carvedilol Buccal Mucoadhesive Patches," Pak. J. Pharm. Sci. 21(3):241-248 (2008).
Elemente des Apparatebause, (Titz, H. (ed.)), pp. 546-669 (Springer-Verlag 1992). (includes partial English translation.).
The United States Pharmacopeia (20th Rev.), pp. 3-4, 12, 16, 955-957, 1023, 1030-1031, 1412, 1451 (USP 1980).
Varanda, F. et al., "Solubility of Antibiotics in Different Solvents. 1. Hydrochloride Forms of Tetracycline, Moxifloxacin, and Ciprofloxacin," Ind. Eng. Chem. Res. 45:6368-6374 (2006).
Phramazeutische Technologie fur Studium und Beruf (Voigt, R. (ed.)), p. 65 (Ullstein Mosby 1995).
Polymer Molecular Weights (Slade, P.E. (ed.), p. 1-8 (Marcel Dekker, Inc. 1975).
Metallic Pigments in Polymers, p. 132 (Rapra Technology Limited 1999).
White, J.G., "In Situ Determination of Delavirdine Mesylate Particle Size in Solid Oral Dosage Forms," Pharmaecutical Research 16(4):545-548 (1999).
Yamamura, K. et al., "Oral Mucosal Adhesive Film Containing Local Anesthetics: In Vitro and Clinical Evaluation," J. Biomed. Mater. Res. (Appl. Biomater.) 43:313-317 (1998).
Pharmazeutische Technologies: Insustrielle Herstellung und Entwicklung von Arzneimitteln (Zimmermann, I. (ed.)), p. 246 (Springer-Verlag 1998).
Modern coating technology systems for paper, film and foil (Shepherd, F. (ed.)), p. 5 (Emap Maclaren Ltd. 1995).
Pharmazeutische Technologie (4th Ed.), (Bauer, K.H. et al. (eds.)), pp. 94-94, 286-287 (Georg Thieme Verlag Stuttgart1993).
Brittian, H.G., "What Is the 'Correct' Method to Use for Particle-Size Determination?," Pharmaceutical Technology 96-98 (Jul. 2001).
"More Solutions to Sticky Problems: A Guide to Getting More From Your Brookfield Viscometer," Brookfield Engineering Laboratories, Inc. (1985).
DeGrande, G., et al., "Specialized Oral Mucosal Drug Delivery Systems: Patches," Drugs and the Pharmaceutical Sciences (Swarbrick, J. (ed.)), Ch. 12, pp. 285-317 (1995).
Polymer Science and Technology (Obewele, R.O. (ed.)), pp. 1-23 (2000).
Etzler, F.M. and Sanderson, "Partilce Size Analysis: a Comparative Study of Various Methods," Part. Part. Syst. Charact. 12: 127-224 (1995).
Roddy, R.E., "A Controlled Trial of Nonoxynol 9 Film to Reduce Male-to-Female Transmission of Sexually Transmitted Diseases," New England J. Med. 339(8):504-510 (1998).
Remington's Pharmaceutical Sciences (18th Ed.) (Gennaro, A.R. (ed.)), Ch. 19, pp. 296-298 (1990).
Etzler, F.M., "Particle Size Analysis: a Comparison of Methods," Polymeric Materials: Science & Engineering 87:335-336 (2002).
Patel, V.F. et al., "Advances in oral transmucosal drug delivery," J. Controlled Release 153:106-116 (2011).

(56) References Cited

OTHER PUBLICATIONS

"Adsorption," Kirk-Othmer Encyclopedia of Chemical Technology (4th Ed.) pp. 493-494 (Wiley 1991).
"Matrix," Webster's Third New International Dictionary of the English Language Unabridged (Gove, P.B. (ed.)) (G. & C. Merriam Company 1968).
Plastic Films (Osborn, K.R. and Jankins, W.A. (eds.), p. 89 (1992).
Martinez, M.N. and Amidon, G.L., "A Mechanistic Approach to Understanding the Factors Affecting Drug Absorption: A Review of Fundamentals," J. Clin. Pharmacol. 42:620-643 (2002).
Amidon, G.L. et al., "A Theoretical Basis for a Biopharmaceutical Drug Classification: The Correlation of in Vitro Drug Product Dissolution and in Vivo Bioavailability," Pharm. Res. 12(3):413-420 (1995).
Anders, R. and Merkle, H.P., "Evaluation of laminated muco-adhesive patches for buccal drug delivery," Int. J. Pharmaceutics 49: 231-240 (1989).
Pharmaceutical Dosage Forms and Drug Delivery Systems (7th Ed.) (Ansel, H.C. et al. (eds.)), p. 66 (1999).
Apicella, A. et al., "poly(ethylene oxide) (PEO) and different molecular weight PEO blends monolithic devices for drug release," Biomaterials 14(2):83-90 (1993).
Pharmazeutische Technologie (5th Ed.) (Bauer, K.H. et al. (eds.)), pp. 208-209 (Stuttgart Jena Lubeck Ulm 1997).
Bowser, T.J. and Wilhelm, L.R., "Modeling Simultaneous Shrinkage and Heat and Mass Transfer of a Thin. Nonporous Film During Drying," J. Food Sci. 60(4):753-757 (1995).
Theory of pharmaceutical systems: vol. II (Carstensen, J.T. (ed.)), pp. 4-9 (1973).
Cassidy, J. P. et al., "Controlled buccal delivery of buprenorphine," J. Controlled Release 25:21-29 (1993).
Eudragit E 100, Eudragit E PO, and Eudragit E 12,5, Technical Information, Evonik Inductries AG, (2012).
Eudragit L 100 and Eudragit S 100, Technical Information, Evonik Inductries AG, (2012).
Europaisches Arzneibuch (3rd Ed.), pp. 142-143 (Deutscher Apotheker Verlag 1997).
European Pharmacopeia (3rd Ed.), p. 134 (1997).
Frankman, O. et al., "clinical Evaluation of C-Film, a Vaginal Contraceptive," J. Int. Med. Res. 3:292-296 (1975).
Friend, D.R., "Polyacrylate resin microcapsules for taste masking of antibiotics," J. Microencapsulation 9(4):469-480 (1992).
Fuller, C.S. et al., "Interactions in poly(ethylene oxide)-hydroxylpropyl methylcellulose blends," Polymer 42:9583-9592 (2001).
Save, T. et al., "Comparative Study of Buccoadhesive Formulations and Sublingual Capsules of Nifedipine," J. Pharm. Pharmacol. 46:192-195 (1994).
Save, T. and Vankitachalam, P., "Studies on Solid Dispersions of Nifedipine," Drug Development and Industrial Pharmacy 18(15):1663-1679 (1992).
Roy, G.M., "Taste Macking in Oral Pharmaceuticals," Pharmaceutical Technology, pp. 84-99 (Apr. 1994).
Guo, J.H. and Cookock, K.M., "Bioadhesive Polymer Buccal Patches for Buprenorphine Controlled Delivery: Solubility Consideration," Drug Development and Industrial Pharmacy 21(7): 2013-2019 (1995).
Mixing in the Process Industries (2nd Ed.) Hamby, N. et al. (eds.)), pp. 3, 115 (Butterworth Heinemann 1997).
Himics, R, and Pineiro, R., "The Importance of Particle Size in Liquid Coatings," Products Finishing 63(2):00329940 (1998).
Handbook of Pharmaceutical Excipients (Rowe, R. et al. (eds.)), pp. 326, 513, 522 (2009).
Ilango, R. et al., "In-Vitro Studies on Buccal strips of Glibenclamide using Chitosan," Indian J. Pharm. Sci. 59 (5):232-235 (1997).
Ishikawa, T. et al., "Preparation and Evaluation of Tablets Rapidly Disintegrating in Saliva Containing Bitter-Taste-Masked Granules by the Compression Method," Chem. Pharm. Bull. 47(10):1451-1454 (1999).
Kaya, S. and Kaya, A., "Microwave drying effects on properties of whey protein isolate edible films," J. Food Engineenng, 43: 91-96 (2000).
U.S. Pat. No. 7,357,891, 90/012,098, Ex Parte Reexamination.
U.S. Pat. No. 7,357,891, IPR2013-00316, Inter Partes Review.
U.S. Pat. No. 7,425,292, 90/012,097, Ex Parte Reexamination.
U.S. Pat. No. 7,425,292, IPR2013-00315, Inter Partes Review.
U.S. Pat. No. 7,666,337, 95/002,171, Inter Partes Reexamination.
U.S. Pat. No. 7,824,588, 95/001,753, Inter Partes Reexamination.
U.S. Pat. No. 7,897,080, 95/002,170, Inter Partes Reexamination.
U.S. Pat. No. 8,017,150, IPR2016-00282, Inter Partes Review.
U.S. Pat. No. 8,603,514, IPR2016-00281, Inter Partes Review.
U.S. Pat. No. 8,652,378, IPR2014-00794, Inter Partes Review.
U.S. Pat. No. 8,765,167, IPR2015-00165, Inter Partes Review.
U.S. Pat. No. 8,765,167, IPR2015-00167, Inter Partes Review.
U.S. Pat. No. 8,765,167, IPR2015-00168, Inter Partes Review.
U.S. Pat. No. 8,765,167, IPR2015-00169, Inter Partes Review.
U.S. Pat. No. 8,603,514, IPR2016-01111, Inter Partes Review.
U.S. Pat. No. 8,017,150, IPR2016-01112, Inter Partes Review.
U.S. Pat. No. 8,603,514, IPR2017-00200, Inter Partes Review.
U.S. Pat. No. 8,603,514, IPR2017-01557, Inter Partes Review.
U.S. Pat. No. 8,603,514, IPR2017-01582, Inter Partes Review.
U.S. Pat. No. 8,900,497, IPR2017-01949, Inter Partes Review.
U.S. Appl. No. 10/074,272, filed Feb. 14, 2002.
U.S. Appl. No. 10/768,809, filed Jan. 30, 2004.
U.S. Appl. No. 10/856,176, filed May 28, 2004.
U.S. Appl. No. 11/092,217, filed Mar. 29, 2005.
U.S. Appl. No. 11/237,525, filed Sep. 28, 2005.
U.S. Appl. No. 11/473,356, filed Jun. 22, 2006.
U.S. Appl. No. 11/517,982, filed Sep. 8, 2006.
U.S. Appl. No. 11/526,996, filed Sep. 26, 2006.
U.S. Appl. No. 11/634,280, filed Dec. 5, 2006.
U.S. Appl. No. 11/639,013, filed Dec. 14, 2006.
U.S. Appl. No. 11/674,223, filed Feb. 13, 2007.
U.S. Appl. No. 11/775,484, filed Jul. 10, 2007.
U.S. Appl. No. 12/102,071, filed Apr. 14, 2008.
U.S. Appl. No. 12/128,950, filed May 29, 2008.
U.S. Appl. No. 12/107,389, filed Apr. 22, 2008.
U.S. Appl. No. 12/171,692, filed Jul. 11, 2008.
U.S. Appl. No. 12/411,505, filed Mar. 26, 2009.
U.S. Appl. No. 12/411,835, filed Mar. 26, 2009.
U.S. Appl. No. 12/575,261, filed Oct. 7, 2009.
U.S. Appl. No. 12/614,928, filed Nov. 9, 2009.
U.S. Appl. No. 12/779,316, filed May 13, 2010.
U.S. Appl. No. 13/035,328, filed Feb. 25, 2011.
U.S. Appl. No. 13/052,655, filed Mar. 21, 2011.
U.S. Appl. No. 13/342,614, filed Feb. 12, 2012.
U.S. Appl. No. 13/096,996, filed Apr. 28, 2011.
U.S. Appl. No. 13/853,237, filed Mar. 29, 2013.
U.S. Appl. No. 13/853,223, filed Mar. 29, 2013.
U.S. Appl. No. 13/853,253, filed Mar. 29, 2013.
U.S. Appl. No. 13/853,276, filed Mar. 29, 2013.
U.S. Appl. No. 13/853,290, filed Mar. 29, 2013.
U.S. Appl. No. 13/890,542, filed May 9, 2013.
U.S. Appl. No. 13/974,376, filed Aug. 23, 2013.
U.S. Appl. No. 13/974,389, filed Aug. 23, 2013.
U.S. Appl. No. 13/974,401, filed Aug. 23, 2013.
U.S. Appl. No. 13/974,413, filed Aug. 23, 2013.
U.S. Appl. No. 14/032,588, filed Sep. 20, 2013.
U.S. Appl. No. 14/195,362, filed Mar. 3, 2014.
U.S. Appl. No. 14/284,019, filed May 21, 2014.
U.S. Appl. No. 14/492,874, filed Sep. 22, 2014.
U.S. Appl. No. 14/572,173, filed Dec. 16, 2014.
U.S. Appl. No. 14/599,803, filed Jan. 19, 2015.
U.S. Appl. No. 14/844,810, filed Sep. 3, 2015.
U.S. Appl. No. 14/945,181, filed Nov. 18, 2015.
U.S. Appl. No. 14/980,836, filed Dec. 28, 2015.
U.S. Appl. No. 15/058,056, filed Mar. 1, 2016.
U.S. Appl. No. 15/144,191, filed May 2, 2016.
U.S. Appl. No. 15/398,398, filed Jan. 4, 2017.
U.S. Appl. No. 15/342,448, filed Nov. 3, 2016.
U.S. Appl. No. 15/438,406, filed Feb. 21, 2017.
U.S. Appl. No. 15/438,458, filed Feb. 21, 2017.

(56) References Cited

OTHER PUBLICATIONS

U.S. Appl. No. 15/634,776, filed Jun. 27, 2017.
U.S. Appl. No. 15/672,228, filed Aug. 8, 2017.
U.S. Appl. No. 15/818,997, filed Nov. 21, 2017.
U.S. Appl. No. 15/865,775, filed Jan. 9, 2018.
U.S. Appl. No. 15/936,241, filed Mar. 26, 2018.
U.S. Appl. No. 15/971,226, filed May 4, 2018.
U.S. Appl. No. 16/163,029, filed Oct. 17, 2018.

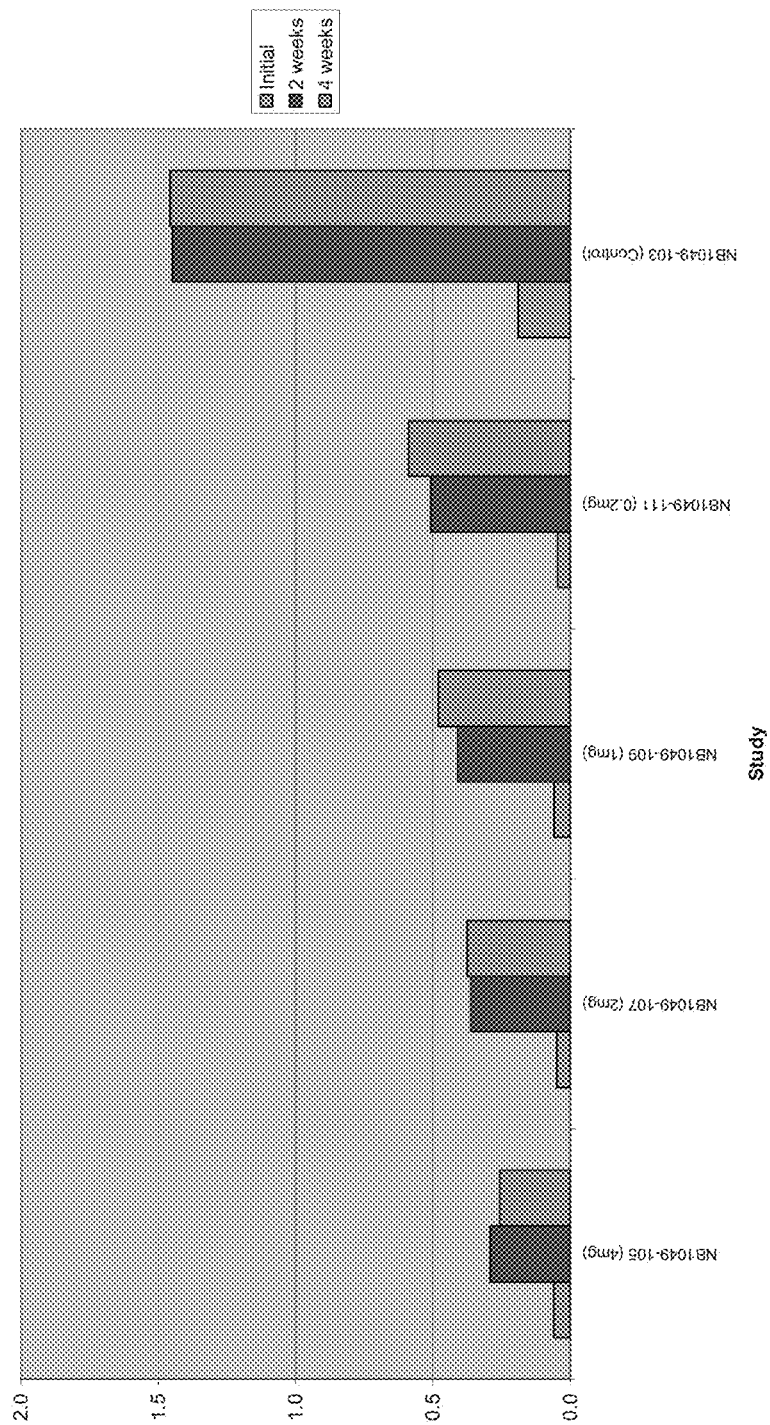

SUBLINGUAL AND BUCCAL FILM COMPOSITIONS

CROSS-REFERENCE TO RELATED APPLICATIONS

This application is a Continuation of U.S. patent application Ser. No. 16/155,100, filed Oct. 9, 2018, which is a Continuation of U.S. patent applications Ser. No. 15/369,101, filed Dec. 5, 2016, which is a Continuation of U.S. patent application Ser. No. 14/196,082, filed Mar. 4, 2014, which issued as U.S. Pat. No. 9,511,033, on Dec. 6, 2016, which is a Continuation of U.S. patent application Ser. No. 13/842,543, filed Mar. 15, 2013, the entire contents of all of which are incorporated by reference herein.

A) This application is a continuation-in-part of U.S. application Ser. No. 13/853,290, filed Mar. 29, 2013, which is a continuation of U.S. application Ser. No. 13/052,655, filed Mar. 21, 2011, which is a continuation of U.S. application Ser. No. 12/411,835, filed Mar. 26, 2009, now U.S. Pat. No. 7,910,031, which is a continuation of U.S. application Ser. No. 12/102,071, filed Apr. 14, 2008, now U.S. Pat. No. 7,824,588, which is a divisional of U.S. application Ser. No. 10/768,809, filed Jan. 30, 2004, now U.S. Pat. No. 7,357,891. application Ser. No. 10/768,809: a) claims benefit to U.S. Provisional Application No. 60/443,741 filed Jan. 30, 2003; b) is a continuation-in-part of International Application No. PCT/US02/32542, filed Oct. 11, 2002; c) is a continuation-in-part of International Application No. PCT/US02/32575, filed Oct. 11, 2002; and d) is a continuation-in-part of International Application No. PCT/US02/32594, filed Oct. 11, 2002. International Application No. PCT/US02/32542: a) claims priority to U.S. Provisional Application No. 60/328,868, filed Oct. 12, 2001; b) claims priority to U.S. Provisional Application No. 371,940, filed Apr. 11, 2002; and c) claims priority to U.S. Provisional Application No. 60/386,937, filed Jun. 7, 2002. International Application No. PCT/US02/32575: a) claims priority to U.S. Provisional Application No. 60/328,868, filed Oct. 12, 2001 and b) claims priority to U.S. Provisional Application No. 60/386,937, filed Jun. 7, 2002. International Application No. PCT/US02/32594: a) claims priority to U.S. Provisional Application No. 60/328,868, filed Oct. 12, 2001; b) claims priority to U.S. Provisional Application No. 60/386,937, filed Jun. 7, 2002; and c) claims priority to U.S. Provisional Application No. 60/414,276, filed Sep. 27, 2002. The entire contents all of the foregoing applications are incorporated herein by reference.

B) This application is also a continuation-in-part of U.S. application Ser. No. 15/672,228, filed Aug. 8, 2017, which is a continuation of U.S. application Ser. No. 14/945,181, filed Nov. 18, 2015, which is a continuation of U.S. application Ser. No. 11/092,217, filed Mar. 29, 2005, which is a continuation of U.S. application Ser. No. 10/074,272, filed Feb. 14, 2002, now U.S. Pat. No. 7,425,292, which claims priority to U.S. Provisional Application No. 60/328,868, filed Oct. 12, 2001. The entire contents all of the foregoing applications are incorporated herein by reference.

This application is a Continuation-in-Part of U.S. patent application Ser. No. 15/699,760, filed Sep. 8, 2017, which is a Continuation of U.S. patent application Ser. No. 15/069,875, filed Mar. 14, 2016, which issued as U.S. Pat. No. 10,034,833, on Jul. 31, 2018, which is a Continuation of U.S. patent application Ser. No. 14/814,461, filed Jul. 30, 2015, which is a Continuation of U.S. patent application Ser. No. 12/537,580, filed Aug. 7, 2009, the entire contents of all of which are incorporated by reference herein.

FIELD OF THE INVENTION

The present invention relates to compositions, methods of manufacture, products and methods of use relating to films containing therapeutic actives. The invention more particularly relates to self-supporting dosage forms which provide an agonist acting alone or in combination with a buffer system to maximize therapeutic absorption of the agonist. Some embodiments also include an antagonist, with the buffer system acting to minimize the absorption of the antagonist. Such compositions are particularly useful for preventing misuse of the active while providing sufficient buccal adhesion of the dosage form.

BACKGROUND OF THE RELATED TECHNOLOGY

Oral administration of two therapeutic actives in a single dosage form can be complex if the intention is to have one active absorbed into the body and the other active remain substantially unabsorbed. For example, one active may be relatively soluble in the mouth at one pH, and the other active may be relatively insoluble at the same pH. Moreover, the absorption kinetics of each therapeutic agent may be substantially different due to differing absorption of the charged and uncharged species. These factors represent some of the challenges in appropriately co-administering therapeutic agents.

Co-administration of therapeutic agents has many applications. Among such areas of treatment include treating individuals who suffer from pain or other medical condition. Such individuals may have a tendency to suffer from serious physical dependence on the therapeutic agent, resulting in potentially dangerous withdrawal effects when the therapeutic agent is not administered to the individual. In order to provide treatment to patients, it is known to provide a reduced level of a therapeutic agent, which provides an effect of treating the condition, but does not provide the "high" that may be provided by the therapeutic agent. The drug provided may be an agonist or a partial agonist, which may provide a reduction in pain or other symptom that the patient is experiencing. However, even though these therapeutic agents provide only a low level of euphoric effect, they are capable of being abused by the individuals parenterally. In such cases, it is desirable to provide a combination of the therapeutic agent with a second therapeutic agent, which may decrease the likelihood of diversion and abuse of the first drug. For example, it is known to provide a dosage of an antagonist in combination with the agonist or partial agonist. The narcotic antagonist binds to a receptor in the brain to block the receptor, thus reducing the effect of the agonist.

One such combination of narcotic agents has been marketed under the trade name Suboxone® as an orally ingestible tablet. However, such combinations in tablet form have the potential for abuse. In some instances, the patient who has been provided the drug may store the tablet in his mouth without swallowing the tablet, then later extract the agonist from the tablet and inject the drug into an individual's body. Although certain antagonists (such as highly water-soluble antagonists) may be used to help reduce the ability to separate the agonist, the potential for abuse still exists. Further, incorporation of an antagonist in combination with the pain-relieving agonist has been found to reduce side effects associated with administration of the agonist, such as constipation and other undesirable effects. It is desired to provide a dosage that cannot be easily removed from the mouth once it has been administered.

There is currently a need for an orally dissolvable film dosage form that provides the desired absorption levels of the agonist and antagonist, while providing an adhesive effect in the mouth, rendering it difficult to remove once placed in the mouth and achieving optimum absorption of the agonist while inhibiting absorption of the antagonist.

SUMMARY OF THE INVENTION

In one embodiment of the present invention, there is provided a self-supporting film dosage composition including: a polymeric carrier matrix; a therapeutically effective amount of an agonist or a pharmaceutically acceptable salt thereof; and a buffer sufficient to maximize the absorption of the agonist.

In another embodiment of the present invention, there is provided a self-supporting film dosage composition including a polymeric carrier matrix, a therapeutically effective amount of an agonist or a pharmaceutically acceptable salt thereof, a buffer sufficient to maximize the absorption of the agonist, and a chelator or antioxidant. In another embodiment of the present invention, there is provided a self-supporting film dosage composition including a polymeric carrier matrix, a therapeutically effective amount of an agonist or a pharmaceutically acceptable salt thereof, a therapeutically effective amount of an antagonist or a pharmaceutically acceptable salt thereof, buffering system; and a chelator or an antioxidant, wherein said buffering system comprises a buffer capacity sufficient to inhibit the absorption of said antagonist during the time which said composition is in the oral cavity of a user.

In another embodiment of the present invention, there is provided a self-supporting film dosage composition including: a polymeric carrier matrix; a therapeutically effective amount of an agonist or a pharmaceutically acceptable salt thereof; a therapeutically effective amount of an antagonist or a pharmaceutically acceptable salt thereof; and a buffering system; where the buffering system possesses a buffer capacity sufficient to inhibit the absorption of the antagonist during the time which the composition is in the oral cavity of a user.

In still another embodiment of the present invention, there is provided a method of treatment, including the steps of: providing a film dosage composition including: a polymeric carrier matrix; a therapeutically effective amount of an agonist or a pharmaceutically acceptable salt thereof; and a buffer in an amount sufficient to maximize the absorption of the agonist; and administering the film dosage composition to a patient.

In other embodiments of the present invention, there is provided a method of treatment, including the steps of: providing a film dosage composition including: a polymeric carrier matrix; a therapeutically effective amount of an agonist or a pharmaceutically acceptable salt thereof; a therapeutically effective amount of an antagonist or a pharmaceutically acceptable salt thereof; a first buffer in an amount sufficient to obtain a local pH of the agonist of about 4 to about 9; a buffer in an amount sufficient to obtain a local pH of the antagonist of about 2 to about 4; and administering the film dosage composition to a user.

In another embodiment of the present invention, there is provided a self-supporting film dosage composition including: a first region including: a first polymeric matrix; a therapeutically effective amount of an agonist or a pharmaceutically acceptable salt thereof; and a first buffering system in an amount sufficient to optimize the absorption of the agonist; a second region including: a second polymeric matrix; a therapeutically effective amount of an antagonist; and a second buffering system in an amount sufficient to inhibit the absorption of the antagonist.

In a further embodiment of the present invention, there is provided an orally dissolving film formulation including a first region including a therapeutically effective amount of an agonist and second region including a therapeutically effective amount of an antagonist, where the formulation provides an in vivo plasma profile having a Cmax of about 0.868-6.94 ng/ml for the agonist and an in vivo plasma profile having a Cmax of about 32.5-260 pg/ml for the antagonist.

In another embodiment of the present invention, there is provided a self-supporting film dosage composition including: a polymeric carrier matrix; a therapeutically effective amount of an agonist or a pharmaceutically acceptable salt thereof; a therapeutically effective amount of an antagonist or a pharmaceutically acceptable salt thereof; and a buffering system sufficient to obtain a local pH of the antagonist of about 2 to about 4.

In an embodiment of the present invention, there is provided a self-supporting film dosage composition including: a polymeric carrier matrix; a therapeutically effective amount of an agonist or a pharmaceutically acceptable salt thereof; a therapeutically effective amount of an antagonist or a pharmaceutically acceptable salt thereof; and a buffering system sufficient to inhibit absorption of the antagonist and optimize absorption of the agonist when the film dosage composition is placed in the mouth of a user.

In another embodiment of the present invention, there is provided a self-supporting film dosage composition including: a first region including: a first polymeric matrix; a therapeutically effective amount of an agonist or a pharmaceutically acceptable salt thereof; and a first buffering system in an amount sufficient to optimize absorption of the agonist when the film dosage composition is placed in the mouth of a user; and a second region including: a second polymeric matrix; a therapeutically effective amount of an antagonist; and a second buffering system in an amount sufficient to inhibit absorption of the antagonist when the film dosage composition is placed in the mouth of a user.

In yet another embodiment of the present invention, there is provided a process of forming a film dosage composition including the steps of: casting a film-forming composition, the film-forming composition including: a polymeric carrier matrix; a therapeutically effective amount of an agonist or a pharmaceutically acceptable salt thereof; a therapeutically effective amount of an antagonist or a pharmaceutically acceptable salt thereof; and a buffer in an amount sufficient to optimize absorption of the agonist and sufficient to inhibit absorption of the antagonist when the film dosage composition is placed in the mouth of a user; and drying the film-forming composition to form a self-supporting film dosage composition.

In still another embodiment of the present invention, there is provided a method of treatment, including the steps of: providing a film dosage composition including: a polymeric carrier matrix; a therapeutically effective amount of an agonist or a pharmaceutically acceptable salt thereof; a therapeutically effective amount of an antagonist or a pharmaceutically acceptable salt thereof; and a buffering system in an amount sufficient to provide an in vivo plasma profile having a Cmax of about 0.624-5.638 ng/ml for the agonist and an in vivo plasma profile having a Cmax of less than 324 pg/ml for the antagonist; and administering the film dosage composition to a user.

In another embodiment of the present invention, there is provided a self-supporting film dosage composition including: a first region including: a first polymeric matrix; a therapeutically effective amount of an agonist or a pharmaceutically acceptable salt thereof; and a first buffering system in an amount sufficient to optimize the absorption of the agonist; a second region including: a second polymeric matrix; a therapeutically effective amount of an antagonist; and a second buffering system in an amount sufficient to inhibit the absorption of the antagonist; where the second region dissolves at a faster rate when placed in the oral cavity of the user than the first region.

In another embodiment of the invention, there is provided a process of forming a film dosage composition including the steps of: casting a first film-forming composition, the first film-forming composition including: a polymeric carrier matrix; a therapeutically effective amount of an agonist or a pharmaceutically acceptable salt thereof; and a buffer in an amount sufficient to optimize absorption of the agonist when the film dosage composition is placed in the mouth of a user; casting a second film-forming composition, the second film-forming composition including: a polymeric carrier matrix; a therapeutically effective amount of an antagonist or a pharmaceutically acceptable salt thereof; and a buffer in an amount sufficient to inhibit absorption of the antagonist when the film dosage composition is placed in the mouth of a user; and laminating the first film-forming composition and the second film-forming composition together to form a self-supporting film dosage composition.

BRIEF DESCRIPTION OF THE DRAWINGS

FIG. 1 shows a graph presenting the results of an EDTA concentration study.

DETAILED DESCRIPTION OF THE PREFERRED EMBODIMENTS

Definitions

As used herein, the term Cmax refers to the mean maximum plasma concentration after administration of the composition to a human subject. As also used herein, the term AUC refers to the mean area under the plasma concentration-time curve value after administration of the compositions formed herein. As will be set forth in more detail below, the term "optimizing the absorption" does not necessarily refer to reaching the maximum absorption of the composition, and rather refers to reaching the optimum level of absorption at a given pH. The "optimum" absorption may be, for example, a level that provides a bioequivalent absorption as administration of the currently available Suboxone® tablet. Thus, if a bioequivalent absorption to Suboxone® is desired, the Cmax of buprenorphine may be about 0.67 to about 5.36 ng/ml at dosages of from 2-16 mg buprenorphine at a given pH. Similarly, an "optimum" AUC of buprenorphine may be about 7.43 to about 59.46 hr*ng/ml at dosages of from 2-16 mg buprenorphine at a given pH. As will be described in more detail below, it has been surprisingly discovered that the absorption of one particular agonist, buprenorphine, can provide an optimum absorption at a local pH of about 3-4 as well as about 5.5-6.5. Thus, one may "optimize" the absorption of buprenorphine by providing a local pH of about 3-4 or about 5.5-6.5.

"Maximizing the absorption" refers to the maximum in vivo absorption values achieved at a local pH of about 4 to about 9.

The term "local pH" refers to the local pH of the region of the carrier matrix immediately surrounding the active agent as the matrix hydrates and/or dissolves, for example, in the mouth of the user.

By "inhibiting" the absorption of an active, it is meant achieving as complete an ionization state of the active as possible, such that little to none of the active is measurably absorbable. For example, at a local pH of 3-3.5, the Cmax of an active such as naloxone for dosage of 0.5 mg to 4.0 mg ranges from 32.5 to 260 pg/ml, and an AUC of naloxone for dosage of 0.5 mg to 4.0 mg ranges from 90.55 to 724.4 hr*pg/ml. It is understood that at a local pH lower than 3.0, further ionization would be expected and thus result in lower absorption.

The term "bioequivalent" means obtaining 80% to 125% of the Cmax and AUC values for a given active in a different product. For example, assuming Cmax and AUC values of buprenorphine for a commercially-available Suboxone® tablet (containing 2 mg buprenorphine and 0.5 mg naloxone) are 0.780 ng/ml and 6.789 hr*ng/ml, respectively, a bioequivalent product would have a Cmax of buprenorphine in the range of 0.624-0.975 ng/ml, and an AUC value of buprenorphine of 5.431-8.486 hr*ng/ml.

It will be understood that the term "film" includes thin films, sheets and wafers, in any shape, including rectangular, square, or other desired shape. The films described herein may be any desired thickness and size such that it may be placed into the oral cavity of the user. For example, the films may have a relatively thin thickness of from about 0.1 to about 10 mils, or they may have a somewhat thicker thickness of from about 10 to about 30 mils. For some films, the thickness may be even larger, i.e., greater than about 30 mils. Films may be in a single layer or they may be multi-layered, including laminated films.

Oral dissolving films generally fall into three main classes: fast dissolving, moderate dissolving and slow dissolving. Fast dissolving films generally dissolve in about 1 second to about 30 seconds in the mouth. Moderate dissolving films generally dissolve in about 1 to about 30 minutes in the mouth, and slow dissolving films generally dissolve in more than 30 minutes in the mouth. Fast dissolving films may consist of low molecular weight hydrophilic polymers (i.e., polymers having a molecular weight between about 1,000 to 9,000, or polymers having a molecular weight below 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, but also have a good level of mucoadhesion. Moderate dissolving films are also flexible, quickly wettable, and are typically non-irritating to the user. For the instant invention, it is preferable to use films that fall between the categories of fast dissolving and moderate dissolving. Such moderate dissolving films provide a quick enough dissolution rate, most desirably between about 1 minute and about 20 minutes, while providing an acceptable mucoadhesion level such that the film is not easily removable once it is placed in the oral cavity of the user.

Inventive films described herein may include one or more agonists or partial agonists. As used herein, the term "agonist" refers to a chemical substance that is capable of providing a physiological response or activity in the body of the user. The films described herein may further include one or more antagonists. As used herein, the term "antagonist" refers to any chemical substance that acts within the body of the user to reduce the physiological activity of another chemical substance. In some embodiments, an antagonist used herein may act to reduce and/or block the physiological activity of the agonist. The actives may be water-soluble, or they may be water-insoluble. As used herein, the term "water-soluble" refers to substances that are at least partially dissolvable in a solvent, including but not limited to water. The term "water-soluble" does not necessarily mean that the substance is 100% dissolvable in the solvent. The term "water-insoluble" refers to substances that are not readily dissolvable in a solvent, including but not limited to water. Solvents may include water, or alternatively may include other polar solvents by themselves or in combination with water.

Inventive Films

The present invention relates to methods of treating pain or other symptoms in an individual while limiting the potential for abuse of the treatment. More desirably, the invention relates to the treatment of physical pain in an individual, for example by administration of an analgesic or other pain-relieving therapeutic agent. One such therapeutic agent that is known to treat pain in individuals which is an agonist such as buprenorphine. However, buprenorphine is known to be a partial agonist and therefore can be abused, and as such it is desired to combine buprenorphine with an antagonist, thereby lessening the potential for abuse by parenteral injection. Such combination of drugs is currently provided via a product marketed under the trade name Suboxone®, which is an orally dissolvable tablet. This tablet which provides a combination of buprenorphine (an opioid agonist) and naloxone (an opioid antagonist). However, even using an antagonist such as naloxone may be abused by a user. Therefore, the present invention provides a method of treating pain or other symptoms in a patient by providing an orally dissolvable film dosage, which provides a bioequivalent effect to Suboxone®. The film dosage further preferably provides buccal adhesion while it is in the user's mouth, rendering it difficult to remove after placement.

The film dosage composition preferably includes a polymeric carrier matrix. Any desired polymeric carrier matrix may be used, provided that it is orally dissolvable. Desirably, the dosage should have enough bioadhesion to not be easily removed and it should form a gel like structure when administered. The orally consumable films are preferably moderate-dissolving in the oral cavity and particularly suitable for delivery of actives, although both fast and sustained release compositions are also among the various embodiments contemplated. In some embodiments, as will be described in more detail below, the inventive combination may include films that have more than one region, where each region has a different dissolution profile.

The films used in the pharmaceutical products may be produced by a combination of at least one polymer and a solvent, optionally including other fillers known in the art. The solvent may be water, a polar organic solvent including, but not limited to, ethanol, isopropanol, acetone, or any combination thereof. In some embodiments, the solvent may be a non-polar organic solvent, such as methylene chloride. The film may be prepared by utilizing a selected casting or deposition method and a controlled drying process. For example, the film may be prepared through controlled drying processes, which include application of heat and/or radiation energy to the wet film matrix to form a viscoelastic structure, thereby controlling the uniformity of content of the film. Such processes are described in more detail in commonly assigned U.S. Pat. No. 7,425,292, the contents of which are incorporated herein by reference in their entirety. Alternatively, the films may be extruded as described in commonly assigned U.S. application Ser. No. 10/856,176, filed on May 28, 2004, and published as U.S. Patent Publication No. 2005/0037055 A1, the contents of which are incorporated herein by reference in their entirety.

The polymer included in the films may be water-soluble, water-swellable, water-insoluble, or a combination of one or more either water-soluble, water-swellable or water-insoluble polymers. The polymer may include cellulose or a cellulose derivative. Specific examples of useful water-soluble polymers include, but are not limited to, polyethylene oxide, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water-insoluble polymers include, but are not limited to, ethyl cellulose, hydroxypropyl ethyl cellulose, cellulose acetate phthalate, hydroxypropyl methyl cellulose phthalate and combinations thereof. For higher dosages, it may be desirable to incorporate a polymer which provides a high level of viscosity as compared to polymers suitable for lower dosages.

As used herein the phrase "water-soluble polymer" and variants thereof refer to a polymer that is at least partially soluble in water, and desirably fully or predominantly soluble in water, or absorbs water. Polymers that absorb water are often referred to as being water-swellable polymers. The materials useful with the present invention may be water-soluble or water-swellable at room temperature and other temperatures, such as temperatures exceeding room temperature. Moreover, the materials may be water-soluble or water-swellable at pressures less than atmospheric pressure. Desirably, the water-soluble polymers are water-soluble or water-swellable having at least 20 percent by weight water uptake. Water-swellable polymers having a 25 or greater percent by weight water uptake are also useful. In some embodiments, films formed from such water-soluble polymers may be sufficiently water-soluble to be dissolvable upon contact with bodily fluids.

Other polymers useful for incorporation into the films include biodegradable polymers, copolymers, block polymers and combinations thereof. It is understood that the term "biodegradable" is intended to include materials that chemically degrade in the presence of a solvent, as opposed to materials that physically break apart (i.e., bioerodable materials). Among the known useful polymers or polymer classes which meet the above criteria are: poly(glycolic acid) (PGA), poly(lactic acid) (PLA), polydioxanes, polyoxalates, poly($\alpha$-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°–347° F. (170°–175° C.); lactide/glycolide 100 L, believed to be 100% glycolide having a melting point within the range of 437°–455° F. (225°–235° C.); lactide/glycolide 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point within the range of 338°–347° F. (170°–175° C.).

The Biodel materials represent a family of various polyanhydrides which differ chemically.

Although a variety of different polymers may be used, it is desired to select polymers that provide mucoadhesive properties to the film, as well as a desired dissolution and/or disintegration rate. In particular, the time period for which it is desired to maintain the film in contact with the mucosal tissue depends on the type of active contained in the composition. Some actives may only require a few minutes for delivery through the mucosal tissue, whereas other actives may require up to several hours or even longer. Accordingly, in some embodiments, one or more water-soluble polymers, as described above, may be used to form the film. In other embodiments, however, it may be desirable to use combinations of water-soluble polymers and polymers that are water-swellable, water-insoluble and/or biodegradable, as provided above. The inclusion of one or more polymers that are water-swellable, water-insoluble and/or biodegradable may provide films with slower dissolution or disintegration rates than films formed from water-soluble polymers alone. As such, the film may adhere to the mucosal tissue for longer periods or time, such as up to several hours, which may be desirable for delivery of certain active components.

Desirably, the individual film dosage has a small size that is between about 0.5-1 inch by about 0.5-1 inch. Most preferably, the film dosage is about 0.75 inches×0.5 inches. The film dosage should have good adhesion when placed in the buccal cavity or in the sublingual region of the user. Further, the film dosage should disperse and dissolve at a moderate rate, that is, between about 1 minute to about 30 minutes, and most desirably between about 10 minutes and about 20 minutes. In some embodiments, however, it may be desired to allow the individual film dosage to dissolve slower, over a period of longer than about 30 minutes. In such slow dissolving embodiments, it is preferable that the film dosage has strong mucoadhesion properties. In other embodiments, however, it may be desirable to use a faster dissolving material, for example between about 1 to about 3 minutes. Further, the film dosage should include components that aid in adhesion to the inner surface of the user's oral cavity, such as the buccal cavity or sublingually. In particular, for dual-layered films, the region including the agonist should have a higher degree of adhesion than the region including the antagonist. In this fashion, the agonist may be released quicker and ingested by the user.

For instance, in some embodiments, the films may include polyethylene oxide alone or in combination with a second polymer component. In some embodiments, the films may include polymers other than polyethylene oxide. The second polymer may be another water-soluble polymer, a water-swellable polymer, a water-insoluble polymer, a biodegradable polymer or any combination thereof. Suitable water-soluble polymers include, without limitation, any of those provided above. In some embodiments, the water-soluble polymer may include hydrophilic cellulosic polymers, such as hydroxypropyl cellulose and/or hydroxypropylmethyl cellulose. Other specific examples of useful water soluble polymers include, but are not limited to, polyethylene oxide (PEO), pullulan, hydroxypropyl cellulose, polydextrose, polyvinyl pyrrolidone, carboxymethyl cellulose, polyvinyl alcohol, sodium alginate, propylene glycol alginate, carrageenan, polyethylene glycol, xanthan gum, tragancanth gum, guar gum, acacia gum, arabic gum, polyacrylic acid, methylmethacrylate copolymer, poloxamer polymers, copolymers of acrylic acid and alkyl acrylate (availale as Pemulen® polymers), carboxyvinyl copolymers, starch, gelatin, pectin, and combinations thereof.

Specific examples of useful water insoluble polymers include, but are not limited to, ethyl cellulose, hydroxypropyl ethyl cellulose, cellulose acetate phthalate, hydroxypropyl methyl cellulose phthalate, acrylic polymers, vinyl acetate, sodium sulphonated polyesters, carboxylated acrylics, trimethylpentanediol/adipic acid/glycerin cross polymer, polyglycerol-2-diisostearate/IPDI copolymer, carboxylated vinyl acetate copolymer, vinylpyrrolicone/vinyl acetate/alkylaminoacrylate terpolymers, vinylpyrrolidone/vinyl acetate copolymer, and combinations thereof.

In accordance with some embodiments, polyethylene oxide may range from about 20% to 100% by weight in the polymer component, more specifically about 30% to about 70% by weight, and even more specifically about 40% to about 60% by weight. In some embodiments, one or more water-swellable, water-insoluble and/or biodegradable polymers also may be included in the polyethylene oxide-based film. Any of the water-swellable, water-insoluble or biodegradable polymers provided above may be employed. The second polymer component may be employed in amounts of about 0% to about 80% by weight in the polymer component, more specifically about 30% to about 70% by weight, and even more specifically about 40% to about 60% by weight.

The molecular weight of the polyethylene oxide also may be varied. In some embodiments, high molecular weight polyethylene oxide, such as about 4 million, may be desired to increase mucoadhesivity of the film. In some other embodiments, the molecular weight may range from about 100,000 to 900,000, more specifically from about 100,000 to 600,000, and even more specifically from about 100,000 to 300,000. In some embodiments, it may be desirable to combine high molecular weight (600,000 to 900,000) with low molecular weight (100,000 to 300,000) polyethylene oxide in the polymer component. Suitable polymers include those described in the applicant's co-pending application, U.S. Publication Number 2008-0260809, the entire contents of which are incorporated by reference herein.

A variety of optional components and fillers also may be added to the films. These may include, without limitation: surfactants; plasticizers; polyalcohols; anti-foaming agents, such as silicone-containing compounds, which promote a smoother film surface by releasing oxygen from the film; thermo-setting gels such as pectin, caragEenan, and gelatin, which help in maintaining the dispersion of components; inclusion compounds, such as cyclodextrins and caged molecules; coloring agents; and flavors. In some embodiments, more than one active component may be included in the film.

Chelators may be included in the films. Applicants have surprisingly discovered that chelators may be employed to reduce or eliminate the oxidation of active ingredients in film compositions. In fact, chelators can be as effective as or even more effective than anti-oxidants in preventing or reducing oxidation of some actives, such as naloxone.

In practice, a chelator is added to the compositions of the present invention in the same manner as any other additive. In certain embodiments, a chelator is added to one or more regions of a multi-region film. In another embodiment, a chelator is added to one or both regions of a dual region film. In these embodiments, the chelator may be the same in each region or may differ between regions.

The chelator may be any chelator known in the art. Chelators have two functional groups that donate a pair of electrons such as =O, —NH2, —COO— and allow ring formation with metal. Examples of chelators include, for example, ethylenediaminetetraacetic acid (EDTA), proteins, polysaccharides, polynucleic acids, glutamic acid, histidine, organic diacids, polypeptides, phytochelatin, hemoglobin, chlorophyll, humic acid, phosphonates, transferrin, desferrioxamine, and combinations thereof. Preferably, the chelator is EDTA or a salt thereof. Salts of EDTA include, for example, EDTA disodium salt, EDTA tetraammonium salt, EDTA tetrasodium salt, EDTA calcium disodium salt, EDTA tetrapotassium salt, EDTA diammonium salt.

In an embodiment of the present invention, the chelator is present in the film dosage compositions in an amount of about 0.1 to about 10% by weight of the total film dosage composition, preferably in an amount of 0.5 to about 7.5%, and more preferable in an amount of about 1 to about 2%.

In an embodiment of the present invention, the weight ratio of antagonist, such as naloxone, to chelator of about 0.2 to 2 to about 2 to 0.5, preferably in a weight ratio of 1 to 2 about 2 to 1.

Antioxidants may be included in the films. Antioxidants may be included in the films. Examples of such antioxidants include phenol antioxidants such as butylhydroxytoluene (BHT) IUPAC name: 2,6-bis(1,1-dimethylethyl)-4-methylphenol) and butylated hydroxyanisole (BHA); propyl gallate, sodium sulfate, citric acid, sodium metabusulfite, ascorbic acid, tocopherol, tocopherol ester derivatives, 2-mercaptobenzimidazole and the like. Among these antioxidants, preferred are ascorbic acid, butylhydroxytoluene (BHT), propyl gallate, sodium sulfite, citric acid, sodium metabisulfite, and combinations thereof. The amount of an antioxidant to be used is preferably 0.1 to 20% by mass and more preferably 0.5 to 10% by mass per the total mass of the film dosage composition.

In an embodiment of the present invention, the film dosage composition either a chelator or an antioxidant. In another embodiment, the film dosage composition includes both a chelator and an antioxidant.

Additives may be included in the films. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all film components.

Further additives may be flow agents and opacifiers, such as the oxides of magnesium aluminum, silicon, titanium, etc. desirably in a concentration range of about 0.02% to about 3% by weight and desirably about 0.02% to about 1% based on the weight of all film components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the texture properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins may be up to about 5% and preferably within the range of about 0.5% to about 2% by weight of the total film composition.

It further may be useful to add silicon dioxide, calcium silicate, or titanium dioxide in a concentration of about 0.02% to about 1% by weight of the total composition. These compounds act as flow agents and opacifiers.

Lecithin is one surface active agent for use in the films described herein. Lecithin may be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB").

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols. If desired, the film may include other additives, such as keratin, or proteins, including proteins that are useful in forming a gel, such as gelatine.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

Suitable coloring agents include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

The films may include one or more additives to provide a taste masking of the active component. For example, the films may include ionic exchange resins, including but not limited to a water-insoluble organic or inorganic matrix material having covalently bound functional groups that are ionic or capable of being ionized under appropriate conditions. The organic matrix may be synthetic (e.g., polymers or copolymers or acrylic acid, methacrylic acid, sulfonated styrene or sulfonated divinylbenzene) or partially synthetic (e.g., modified cellulose or dextrans). The inorganic matrix may be, for example, silica gel modified by the addition of ionic groups. Most ion exchange resins are cross-linked by a crosslinking agent, such as divinylbenzene.

Anti-foaming and/or de-foaming components may also be used with the films. These components aid in the removal of air, such as entrapped air, from the film-forming compositions. Such entrapped air may lead to non-uniform films. Simethicone is one particularly useful anti-foaming and/or de-foaming agent. The present invention, however, is not so limited and other anti-foam and/or de-foaming agents may suitable be used.

As a related matter, simethicone and related agents may be employed for densification purposes. More specifically, such agents may facilitate the removal of voids, air, moisture, and similar undesired components, thereby providing denser, and thus more uniform films. Agents or components which perform this function can be referred to as densification or densifying agents. As described above, entrapped air or undesired components may lead to non-uniform films.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films, the mixing step may be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles during and after mixing.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Any other optional components described in commonly assigned U.S. Pat. No. 7,425,292 and U.S. application Ser. No. 10/856,176, referred to above, also may be included in the films described herein.

When the dosage form includes at least one antagonist in addition to the agonist, it may be desired to control the release of the antagonist, so as to minimize or wholly prevent the absorption of the antagonist from the dosage form when taken orally. In this fashion, the antagonist may be released faster and a larger proportion of it may be present as the ionized form in solution, thereby lessening the likelihood of its absorption in the body. Desirably, the dosage form is a self-supporting film composition, which is placed into the oral cavity of the user. In a dosage form that is to be placed in the oral cavity, it is desired to absorb the agonist buccally, so as to provide rapid absorption of the agonist into the body of the user. At the same time, it may be desired to inhibit or reduce absorption of any antagonist buccally, thereby allowing the antagonist to be swallowed and destroyed in the stomach, or in some cases absorbed in the colon. Inhibiting the absorption of an antagonist may alternatively be achieved via physical means, such as by encapsulating the antagonist in a material that blocks absorption. It is desired, however, to reduce the absorption of the antagonist by chemical means, such as by controlling the local pH of the dosage form.

It has been found that by controlling the local pH of the dosage form, the release and/or absorption of the actives therein may be controlled. For example, in a dosage that includes an amount of an agonist, the local pH may be controlled to a level that optimizes its release and/or absorption into the oral cavity of the user. In dosages incorporating an amount of an agonist and an amount of an antagonist, the local pH may be controlled to a level that maximizes the release and/or oral absorption of the agonist while simultaneously minimizing the release and/or oral absorption of the antagonist. For example, the film dosage may include distinct regions, one region including an agonist and the other region including an antagonist, where the local pH of each region is optimized for the desired effect.

The dosage form preferably includes a combination of an agonist and an antagonist, while the dosage has a controlled local pH. It should be understood that the present invention is not limited to the use of any one particular agonist and/or antagonist, and any agonist (or partial agonist) and any antagonist may be incorporated into the present invention. The agonist and optional antagonist should be selected from those agonists and antagonists that are useful in treating the particular symptom being treated. The inventive films discussed herein are best suited for agonists and/or antagonists that are basic in nature. Suitable agonists (and/or partial agonists) may include buprenorphine (pKa=8.42), sufentanil (pKa=8.0), morphine (pKa=8.0), fentanil (pKa=8.4), alfentanil (pKa=6.5), pethidine (pKa=8.7), apomorphine (pKa=8.9), alphaprodine (pKa=8.7), remifentanil (pKa=7.0), methadone (pKa=9.2), codeine (pKa=8.2), dihydrocodeine (pKa=9.4), morphine (pKa=8.0), oxycodone (pKa=8.53), oxymorphone (pKa=8.17), tramadol (pKa=9.41), or pharmaceutically acceptable salts thereof. Suitable antagonists (and/or partial antagonists) may include naloxone, naltrexone, nalorphine and levallorphan, or therapeutically acceptable salts thereof.

As discussed above, the local pH of the dosage is preferably controlled to provide the desired release and/or absorption of the agonist and antagonist. Suitable agonists may have a pKa of about 5 to about 9.5, and most preferably from about 8.0 to about 9.0. Suitable antagonists may have a pKa of about 6.0 to about 9.0, and most preferably about 7.0 to about 9.0. For example, naloxone has a pKa of about 7.94.

According to pH partition theory, one would expect that saliva (which has a local pH of about 6.5) would maximize the absorption of both actives. As generally understood, absorption of an active depends on the available unionized form of the active. Thus, as the local pH of the surrounding environment is lowered, basic actives will be more ionized, and less will be available for absorption. For an active which has a pKa of about 8, one would expect a higher level of absorption to occur at a local pH level of about 6.5, whereas a lower level of absorption should occur at a local pH of about 3.5, since most of the active would be ionized. As will be described in more detail in the Examples below, controlling the local pH of the film compositions of the present invention provides a system in which the desired release and/or absorption of the components is achieved.

In one embodiment, the dosage form is a self-supporting film. In this embodiment, the film dosage includes a polymer carrier matrix, a therapeutically effective amount of an agonist or a pharmaceutically acceptable salt thereof, and a buffer. Preferably, the agonist is a partial agonist, and most desirably the agonist is an opioid agonist, such as buprenorphine. The buffer is preferably capable of providing a local pH of the composition within a range that provides a controllable level and desirably an optimal treatment level of absorption of the agonist. For example, it may be desired to provide an absorption of buprenorphine that is bioequivalent to a Suboxone® tablet.

It has been surprisingly discovered by the Applicants that certain agonists, such as buprenorphine, are capable of being suitably absorbed when the local pH of the film composition is either between about 3 to about 4 or between about 5 to about 9. Thus, the local pH for the film including the agonist may be either from about 3 to about 4 or from about 5 to about 9. To provide a maximum absorption of buprenorphine, for example, the local pH of the film composition may be about 5.5. To provide an absorption of buprenorphine that is bioequivalent to the Suboxone® tablet, the local pH of the film composition may be about 6 to about 7. The resulting dosage is a film composition that allows for a rapid and effective release of the agonist (such as buprenorphine) into the oral cavity of the user. At the same time, the film composition desirably has a sufficient adhesion profile, such that the film cannot easily be removed, or cannot be removed at all, from the oral cavity of the user once it has been placed into the cavity. Full release of the agonist may take place within less than about thirty minutes, e.g., within about 10 minutes to about 30 minutes and preferably remains in the oral cavity for at least 1 minute and desirably about 1 to about 30 minutes.

It may be desirable to combine the opioid agonist (or partial agonist) in the film composition with an opioid antagonist or a pharmaceutically acceptable salt thereof. The agonist and antagonist may be dispersed throughout the dosage separately or the agonist and antagonist may be separately dispersed in individual film regions. Most desirably the antagonist includes naloxone, but any suitable antagonist may be selected as desired. The antagonist may optionally be water-soluble, so as to render separation of the antagonist and agonist difficult, thereby lessening the potential for diversion abuse of the agonist.

As with a film including an agonist, a film including an agonist and an antagonist is desirably pH-controlled through the inclusion of a buffer. At the desired local pH level of the agonist and the antagonist, optimal absorption of the agonist may be achieved while the absorption of the antagonist may be greatly inhibited.

The film may contain any desired level of self-supporting film forming polymer, such that a self-supporting film composition is provided. In one embodiment, the film composition contains a film forming polymer in an amount of at least 25% by weight of the composition. The film forming polymer may alternatively be present in an amount of at least 50% by weight of the composition, and desirably in a range of about 25% to about 75%, and most desirably from about 30% to about 50% by weight of the composition. As explained above, any film forming polymers may be used as desired.

Any desired level of agonist and optional antagonist may be included in the dosage, so as to provide the desired therapeutic effect. In one particular embodiment, the film composition includes about 2 mg to about 16 mg of agonist per dosage. More desirably, the film composition includes about 4 mg to about 12 mg of agonist per dosage. If desired, the film composition may include about 0.5 mg to about 5 mg of antagonist per dosage. More desirably, the film composition includes about 1 mg to about 3 mg of antagonist per dosage. If an antagonist is incorporated into the film, the film composition may include the antagonist in a ratio of about 6:1-2:1 agonist to antagonist. Most desirably, the film composition contains about 4:1 agonist to antagonist per dosage. For example, in one embodiment, the dosage includes an agonist in an amount of about 12 mg, and includes an antagonist in an amount of about 3 mg.

The film compositions further desirably include at least one buffer so as to control the local pH of the film composition. Any desired level of buffer may be incorporated into the film composition so as to provide the desired local pH level. The buffer is preferably provided in an amount sufficient to control the release from the film and/or the absorption into the body of the agonist and the optional antagonist. In a desired embodiment, the film composition includes buffer in a ratio of buffer to agonist in an amount of from about 2:1 to about 1:5 (buffer:agonist). The buffer may alternatively be provided in a 1:1 ratio of buffer to agonist. A film composition including an antagonist preferably has a local pH of about 2 to about 4. Any buffer may be used as desired. In some embodiments, the buffer may include sodium citrate, citric acid, succinic acid, malic acid, phosphoric acid, boric acid, and combinations thereof. The buffer may include a buffering system including a combination of components, such as Citric Acid/Sodium Citrate, Succinic Acid/Monosodium Succinate, Glycine/SodiumGlycine, Malic Acid/Sodium Malate, Phosphoric Acid/Sodium Phosphate, Fumaric Acid/Sodium Fumarate, Monosodium Phosphate/Disodium Phosphate, and Boric Acid/Sodium Borate.

In this embodiment, the resulting film composition includes a polymer matrix, an agonist, and an optional antagonist, while the film composition has a controlled local pH to the level desired. The buffer is desirably present in an amount to provide a therapeutically adequate absorption of the agonist, while simultaneously limiting or preventing substantial absorption of the antagonist. Controlling of the local pH allows for the desired release and/or absorption of the components, and thus provides a more useful and effective dosage.

The film dosage composition may include a polymer carrier matrix, a therapeutically effective amount of agonist, a therapeutically effective amount of antagonist, and a buffering system. A "therapeutically effective amount" of an antagonist is intended to refer to an amount of the antagonist that is useful in diverting abuse of the agonist by a user. The buffering system may include a buffer in addition to a solvent. The buffering system desirably includes a sufficient level of buffer so as to provide a desired local pH level of the film dosage composition.

In addition to a desired local pH level, the buffer desirably has a buffer capacity sufficient to maintain ionization of the optional antagonist during the time that the composition is in the oral cavity of a user. Maintaining ionization of the antagonist serves to limit the absorption of the antagonist, and thus provide the desired control of the antagonist. While the ionization of the antagonist is limited, the ionization of the agonist may not be so limited. As such, the resulting dosage form provides absorption of the agonist to the user, while sufficiently reducing and/or preventing absorption of the antagonist.

In other embodiments, the film dosage composition of the present invention may include an agonist in a sufficient amount so as to provide a release profile bioequivalent to a tablet containing a higher amount of the agonist. By providing a film dosage composition with an agonist and simultaneously controlling the local pH of the film dosage composition, an effective release and absorption of the agonist may be achieved with less of the agonist present in the dosage. For example, the film dosage composition may include an agonist in an amount that is at least 1.5 times less than the amount of the agonist required in a tablet, but still provides a bioequivalent release profile. In some embodiments, the agonist may be a partial agonist. In some embodiments the agonist may be an opioid agonist. In desired embodiments, the agonist includes buprenorphine or a pharmaceutically acceptable salt thereof.

The film dosage composition including an agonist, may be configured to provide an in vivo plasma profile having a mean maximum plasma concentration (Cmax) in a desired range. For example, the desired Cmax may be a bioequivalent level to that of a Suboxone® tablet. It has been discovered by the Applicants that controlling the Cmax of the film composition allows one to control the absorption of the active (such as an agonist) into the user. The resulting film composition is more effective and suitable for delivery to a user.

In one embodiment, the Cmax of the film composition may be about 6.4 ng/ml or less. If desired, the Cmax of the film composition may be less than about 5.2 ng/ml, less than about 3.8 ng/ml, less than about 1.9 ng/ml, or less than about 1.1 ng/ml, depending on the desired dosage level. In such embodiments, the agonist may be present in an amount of from about 2 mg to about 16 mg per dosage, or, if desired about 4 mg to about 12 mg per dosage. The agonist may include buprenorphine or a pharmaceutically acceptable salt thereof.

It has further been discovered that, by controlling the mean area under the curve (AUC) value of the film composition, a more effective dosage form may be provided. In one embodiment, the film composition may include a mean AUC value of about 6.8 hr·ng/ml or greater. Alternatively, the film composition may include a mean AUCinf value of from about 6.8 hr·ng/ml to about 66 hr·ng/ml.

As explained above, the film compositions may include an optional antagonist. When the film composition includes a combination of agonist and antagonist, the film composition may be configured to provide a particular Cmax and/or AUC for the antagonist. For example, when a buprenorphine agonist and a naloxone antagonist are incorporated into the film composition, the naloxone may be configured to provide a Cmax of less than about 400 pg/ml, less than about 318 pg/ml, less than about 235 pg/ml, less than about 92 pg/ml or less than about 64 pg/ml. In such films, the naloxone may provide a mean AUC value of less than about 1030 hr·ng/ml.

In formulations which include an agonist in combination with an antagonist, the film composition may be prepared to provide a desired Cmax and/or AUC value for each of the agonist and antagonist. For example, a dosage having 16 mg of agonist and 4 mg of antagonist may provide an in vivo plasma profile having a Cmax of less than about 6.4 ng/ml for the agonist and an in vivo plasma profile having a Cmax of less than about 400 pg/ml for the antagonist. Such formulation may also provide an AUC value of more than about 6.8 hr·ng/ml for the agonist. If desired, the formulation may provide an AUCinf value of less than about 1030 hr·pg/ml for the antagonist. Bioequivalence levels are set forth in more detail in the Examples discussed below. Such compositions may include the agonist and the antagonist in any desired amount, and in a preferred embodiment, the composition includes about 2 mg to about 16 mg of the agonist per dosage and about 0.5 mg to about 4 mg of the antagonist per dosage. Most desirably, the agonist and antagonist are present in amounts of about 4:1 by weight agonist to antagonist.

In one particular embodiment, there may be provided a self-supporting film dosage composition including more than one region (referred to as a "dual-film product" or a "dual-region product"). The multiple regions may be disposed on top of each other, to the side of each other, or disposed internally of each other. For example, the dosage composition may include two separate regions, disposed in such a configuration where the first region is on top of the second region, or vice versa. If desired, the two regions may be laminated to each other so as to provide a single dosage form. In such embodiments, the first region may be dried prior to laminating any additional regions thereto. Similarly, the second region may be dried prior to laminating the first region thereto. Alternatively, either the first or second region may be at least partially dried prior to laminating any additional regions thereto.

In such multi-region embodiments, there is provided a first region, which includes a first polymeric matrix and a therapeutically effective amount of an agonist. The agonist may be a partial agonist, and the agonist may be an opioid agonist. One such opioid agonist includes buprenorphine, but any desired agonist may be used to treat the particular symptom desired. The first region desirably includes a first buffering system in an amount sufficient to provide a local pH of the agonist so as to optimize the release and/or absorption of the agonist. The first region may be in communication with a second region. The second region may include a second polymeric matrix and a therapeutically effective amount of an antagonist. One such antagonist includes naloxone, but any desired antagonist may be used as desired. The second region may further include a second buffering system in an amount sufficient to provide a local pH of the antagonist so as to inhibit the absorption of the antagonist. In some embodiments, it may be desirable to have one region be dissolved at a faster rate than the second region when it is placed into the mouth of the user. For example, it may be desired to have the region including an antagonist dissolve at a faster rate than the region including an agonist, or vice versa.

In such multi-region film dosages, the first and second regions may work in cooperation to provide a desired absorption profile of the agonist and the antagonist. For example, the first buffering system may be present in an amount sufficient to provide increased absorption of the agonist, while the second buffering system is present in an amount sufficient to provide a decreased absorption of the antagonist. In some embodiments, the first buffering system may be present in an amount sufficient to provide a local pH of the first region so as to provide an optimum absorption of the agonist, i.e., of from either about 3 to about 4 or of from about 4 to about 9, and more specifically from about 6 to about 9. In some embodiments, the second buffering system may be present in an amount sufficient to provide a local pH of the second region of from about 2 to about 4, and more specifically about 2 to about 3. For a multi-region film dosage including buprenorphine in the first region and naloxone in the second region, the local pH of the buprenorphine region is desirably either from about 3 to about 4 or from about 5.5 to about 6.5, and the local pH of the naloxone region is about 2.0 to about 3.0.

Depending on the particular agonist and antagonist incorporated in the dosage, the desired local pH level for each region may be greater or lower so as to optimize absorption of the agonist while inhibiting absorption of the antagonist. Generally, the local pH of the agonist-containing region is desirably between about 4 to about 9, and most desirably about 6 to about 9. The local pH for the antagonist-containing region is most desirably about 2 to about 4. Again, however, it will be understood that the particular agonist incorporated into the dosage may be more optimally absorbed at a higher or lower pH.

The first and second buffering systems may be the same or they may be different. Additionally, the first polymeric matrix and the second polymeric matrix may be the same or they may be different. Any desired levels of agonist and antagonist may be provided, and desirably the dosage composition includes about 2 mg to about 16 mg of the agonist and about 0.5 mg to about 4 mg of the antagonist per dosage unit. More desirably, the dosage composition includes about 4 mg to about 12 mg of the agonist and about 1 mg to about 3 mg of the antagonist per dosage unit.

The first and second regions may be formed together in any desired means. In one embodiment, the second region may be coated, sprayed, or placed onto at least one surface of the first region. Alternatively, the first and second regions may be co-extruded. In some embodiments, the first and second regions may be laminated to each other by means of a suitable composition. Further, the first region may be formed first, and then subsequently dipped into a solution of a wet composition, which is then allowed to dry and form the second region. As will be understood by one of ordinary skill in the art, the first region may include the antagonist while the second region includes the agonist. Further, both regions may include a desired amount of agonist and antagonist so as to provide a desired release and absorption.

The first region may include more components by weight than the second region, or vice versa. For example, the first region may have a total weight that is more than the total weight of the second region, or vice versa. Alternatively, the first and second regions may include the same amount of components by weight.

In another embodiment, there may be provided a self-supporting film dosage composition having more than one region, where each region includes a polymeric matrix and a water-soluble and/or a water-insoluble active. The dosage composition preferably includes a therapeutically effective amount of a water-soluble active and a therapeutically effective amount of water-insoluble active. Each region preferably includes a buffer in an amount sufficient to control the absorption profiles of the water-soluble and water-insoluble actives in each region, depending on the desired level of absorption of the active desired. In one desired embodiment, a first buffer is present in the first region in an amount sufficient to obtain a local pH of one region of about 2 to about 4, while a second buffer is present in the second region in an amount sufficient to obtain a local pH of the second region of about 4 to about 9.

The present invention provides a method of treating various problems in a patient, including, for example physical pain experienced by a patient. Desirably, the patient is treated by providing a dosage to the patient, which provides an effective release of therapeutic active but simultaneously provides a suitable adhesion so that the dosage cannot be easily removed. The dosage forms provided herein are particularly useful in preventing diversion of a drug. In one method of treatment, an orally dissolvable film composition is provided to a patient.

Depending on the particular symptom sought to be treated, the film composition may include one or more particular active components. In one embodiment, the film composition includes a polymer carrier matrix and a therapeutically effective amount of an agonist. Desirably the agonist is a partial agonist. For some types of pain, the agonist may be an opioid agonist, such as buprenorphine or a pharmaceutically acceptable salt thereof. The film composition preferably includes a buffer in an amount sufficient to control the local pH of the film composition. Any buffer or buffering system may be used, including those listed above. Desirably, the local pH of the film composition including an agonist is buffered to be about 4 to about 9, depending on the particular agonist included in the composition. In some embodiments, such as when the agonist is buprenorphine, the desired local pH is about 5 to about 6.5, and most desirably the local pH is about 5.5 to about 6.5. At this level, the absorption of the agonist may be optimized. To treat the pain, the film composition is administered to the patient, most desirably into the oral cavity of the patient, such as through buccal absorption.

If desired, the composition may include a therapeutically effective amount of an antagonist. As explained above, the combination of an agonist and antagonist may help minimize potential abuse of the agonist. The antagonist may be any desired antagonist, and in one embodiment includes naloxone or a pharmaceutically acceptable salt thereof. The film composition is preferably administered to patient through the oral cavity of the patient, but may be administered in any desired means. The orally dissolvable film composition is then allowed to dissolve in the oral cavity of the patient for a sufficient time so as to release the active(s) therein. In some embodiments, the film composition may remain in the oral cavity for at least 30 seconds, and in some embodiments may remain in the oral cavity for at least 1 minute. After the film composition is placed into the oral cavity of the patient, the film preferably becomes sufficiently adhered so as to render its removal difficult. After the film composition has been administered to the patient, the active(s) are sufficiently released from the composition and allowed to take effect on the patient.

In embodiments where there is a dual-region film composition, the administration of the dosage may have regions of differing dissolution rates. For example, the first region of the film composition may include an agonist and a moderate dissolving polymer. Desirably, the first region remains in the oral cavity for at least one minute, and up to about 30 minutes. The second region, which may include an antagonist, desirably contains a fast dissolving polymer. As such, the second region dissolves within less than one minute, thereby releasing the antagonist into the body where it is ingested and ionized. In this way, the antagonist is swallowed, thereby avoiding buccal absorption. However, the antagonist is still present in the film composition before administration so as to limit potential abuse of the drug should a user attempt to extract the agonist from the composition.

The film compositions of the present invention may be formed via any desired process. Suitable processes are set forth in U.S. Pat. Nos. 7,425,292 and 7,357,891, the entire contents of which are incorporated by reference herein. In one embodiment, the film dosage composition is formed by first preparing a wet composition, the wet composition including a polymeric carrier matrix, a therapeutically effective amount of an agonist, and a buffer in an amount sufficient to control the local pH of the composition to a desired level. The wet composition is cast into a film and then sufficiently dried to form a self-supporting film composition. The wet composition may be cast into individual dosages, or it may be cast into a sheet, where the sheet is then cut into individual dosages. The agonist may be a partial agonist. If desired, the wet composition may include a therapeutically effective amount of an antagonist. In some embodiments, especially in single-region dosages, the local pH of the film may be about 2 to about 4, and more particularly between about 3 to about 4.

The agonist and the optional antagonist are preferably selected to treat a particular problem, such as treatment of physical pain suffered by a patient. For example, the agonist may include buprenorphine or a pharmaceutically acceptable salt thereof, while the antagonist may include naloxone or a pharmaceutically acceptable salt thereof. The film composition includes at least one buffer or buffering system so as to control the local pH of the agonist and antagonist to desired levels. In this fashion, the absorption of the agonist may be optimized while the absorption of the antagonist may be inhibited. In one desired embodiment, the inventive film provides an absorption of the agonist that is bioequivalent to that of a Suboxone® tablet.

If the desired optimum absorption of the agonist is to provide a bioequivalent absorption to that of a Suboxone® tablet, the local pH of the film composition should provide a local pH of the agonist of either between about 3 to about 4 or between about 5.5 to about 6.5, and a local pH of the antagonist of between about 2 to about 4. In a film composition including only one region with the agonist and antagonist, the local pH is desirably about 3 to about 4 to provide a bioequivalent absorption to the Suboxone® tablet.

Active ingredients in pharmaceutical compositions can degrade and lose their effectiveness when included in a pharmaceutical composition and stored. In certain cases, the active ingredient may oxidize into a form that is, for example, less bioavailable.

To minimize or prevent oxidation of the active, the film may be manufacture in whole or in part under an inert gas environment. A preferred inert gas is nitrogen.

Applicants have surprisingly discovered that chelators may be employed to reduce or eliminate the oxidation of active ingredients in film compositions. In fact, chelators are more effective than anti-oxidants in preventing or reducing oxidation of some actives, such as naloxone.

In practice, a chelator is added to the compositions of the present invention in the same manner as any other additive. In certain embodiments, a chelator is added to one or more regions of a multi-region film. In another embodiment, a chelator is added to one or both regions of a dual region film. In these embodiments, the chelator may be the same in each region or may differ between regions.

EXAMPLES

Example 1

Composition of Buprenorphine/Naloxone Films at Various Strengths

Film strips including a combination of buprenorphine and naloxone were prepared. Four different strength film compositions were prepared, which include a ratio of buprenorphine to naloxone of 16/4, 12/3, 8/2, and 2/0.5. The compositions are summarized in Table 1 below.

TABLE 1

Various Compositions of Film Dosages

| Components | Buprenorphine/Naloxone Films Unit Formula (mg per film strip) Buprenorphine/Naloxone Ratios | | | |
|---|---|---|---|---|
| | 16/4 | 12/3 | 8/2 | 2/0.5 |
| Active Components | | | | |
| Buprenorphine HCl | 17.28 | 12.96 | 8.64 | 2.16 |
| Naloxone HCl Dihydrate | 4.88 | 3.66 | 2.44 | 0.61 |
| Inactive Components | | | | |
| Polyethylene Oxide, NF (MW 200,000) | 27.09 | 20.32 | 13.55 | — |
| Polyethylene Oxide, NF (MW 100,000) | 12.04 | 9.03 | 6.02 | 19.06 |
| Polyethylene Oxide, NF (MW 900,000) | 4.82 | 3.62 | 2.41 | 2.05 |
| Sugar Alcohol | 12.04 | 9.03 | 6.02 | 5.87 |
| Flavor | 6.0 | 4.5 | 3.0 | 2.4 |
| Citric Acid, USP | 5.92 | 4.44 | 2.96 | 2.96 |
| HPMC | 4.22 | 3.16 | 2.11 | 2.34 |
| Sweetener | 3.0 | 2.25 | 1.5 | 1.2 |
| Sodium Citrate, anhydrous | 2.68 | 2.01 | 1.34 | 1.34 |
| Colorant | 0.03 | 0.02 | 0.01 | 0.01 |
| Total (mg) | 100 | 75 | 50 | 40 |

Example 2

Absorption Studies for Suboxone® Tablets

Various film and tablet products were prepared and tested for absorption data, including Cmax and AUC absorption levels. The products tested included Suboxone® tablets made with either 2 mg or 16 mg buprenorphine as well as either 0.5 mg or 4.0 mg naloxone. For 16 mg buprenorphine tablets, two 8 mg buprenorphine tablets were combined together to provide the level of components of a 16 mg buprenorphine tablet. In instances where a 12 mg buprenorphine tablet was evaluated, this dosage was obtained by combining one 8 mg buprenorphine tablet and two 2 mg buprenorphine tablets. These products were tested for absorption levels, with the amounts listed in Table 2 below.

TABLE 2

Absorption Data for Suboxone® products

| Sample | C max | AUC |
|---|---|---|
| Buprenorphine (2 mg) Suboxone ® Tablet | 0.780 ng/ml | 6.789 hr * ng/ml |
| Naloxone (0.5 mg) Suboxone ® Tablet | 51.30 pg/ml | 128.60 hr * pg/ml |
| Buprenorphine (16 mg) Suboxone ® Tablet | 4.51 ng/ml | 44.99 hr * ng/ml |
| Naloxone (4 mg) Suboxone ® Tablet | 259.00 pg/ml | 649.60 hr * pg/ml |

Using the data from Table 2, absorption data for the Suboxone® tablets for other levels of buprenorphine and naloxone are set forth in Table 2A below.

TABLE 2A

Absorption Data for Suboxone® tablets

| Sample | C max | AUC |
|---|---|---|
| Buprenorphine (4 mg) Suboxone ® Tablet | 1.35 ng/ml | 12.25 hr * ng/ml |
| Naloxone (1 mg) Suboxone ® Tablet | 80.97 pg/ml | 203 hr * pg/ml |
| Buprenorphine (8 mg) Suboxone ® Tablet | 2.29 ng/ml | 23.17 hr * ng/ml |
| Naloxone (2 mg) Suboxone ® Tablet | 140.31 pg/ml | 351.8 hr * pg/ml |
| Buprenorphine (12 mg) Suboxone ® Tablet | 3.23 ng/ml | 34.08 hr * ng/ml |
| Naloxone (3 mg) Suboxone ® Tablet | 199.7 pg/ml | 500.6 hr * pg/ml |

Example 3

Evaluation of Bioequivalence of Suboxone® Tablets

Using the data generated for Suboxone® tablets in Table 2 above, acceptable bioequivalence ranges are generated so as to provide an equivalent treatment level as the Suboxone® tablet. As currently understood, a product provides a bioequivalent effect if it provides absorption levels between about 80% to about 125% of the Suboxone® tablet. Absorption in this range is considered to be bioequivalent.

TABLE 3

Acceptable Bioequivalence Ranges for Suboxone ® Tablets (80 to 125%)

| Description of Sample | C max | AUC |
|---|---|---|
| Buprenorphine 2 mg | 0.624 to 0.975 ng/ml | 5.431 to 8.486 hr * ng/ml |
| Naloxone 0.5 mg | 41.04 to 64.13 pg/ml | 102.88 to 160.75 hr * pg/ml |
| Buprenorphine 16 mg | 3.608 to 5.638 ng/ml | 35.992 to 56.238 hr * ng/ml |
| Naloxone 4 mg | 207.20 to 323.75 pg/ml | 519.68 to 812.00 hr * pg/ml |

Thus, to be considered bioequivalent to the Suboxone® tablet, the Cmax of buprenorphine is between about 0.624 and 5.638, and the AUC of buprenorphine is between about 5.431 to about 56.238. Similarly, to be considered bioequivalent to the Suboxone® tablet, the Cmax of naloxone is between about 41.04 to about 323.75, and the AUC of naloxone is between about 102.88 to about 812.00.

Example 4

Composition of Buprenorphine Films at Various Strengths

Film strips including a buprenorphine were prepared. Two different strength film compositions were prepared, which include buprenorphine in a dosage amount of 8 mg and in a dosage amount of 2 mg. The compositions are summarized in Table 4 below.

TABLE 4

Various Compositions of Film Dosages

| Components | Buprenorphine Films Unit Formula (mg per film strip) | |
|---|---|---|
| Buprenorphine | 8.64 | 2.16 |
| Inactive Components | | |
| Polyethylene Oxide, NF (MW 100,000) | 17.66 | 21.87 |
| Polyethylene Oxide, NF (MW 900,000) | 2.17 | 2.35 |
| Sugar Alcohol | 5.43 | 6.72 |
| Flavor | 2.8 | 2.8 |
| HPMC | 1.9 | 2.69 |
| Sweetener | 1.2 | 1.2 |
| Colorant | 0.2 | 0.2 |
| Total (mg) | 40 | 40 |

Example 5

Cmax and AUCinf Levels for Film Strips Incorporating Buprenorphine

Five film dosage compositions were prepared, each including buprenorphine in a dosage of from 2 mg to 16 mg. Table 5 below sets forth Cmax and AUCinf levels for various dosage levels of film compositions including buprenorphine.

TABLE 5

Cmax and AUCinf Levels for Film Strips Incorporating Buprenorphine

| Buprenorphine | Cmax | AUCinf |
|---|---|---|
| 2 mg | 0.7-1.07 ng/ml | 6.8-9.5 hr · ng/ml |
| 4 mg | 1.2-1.84 ng/ml | 11.2-16.7 hr · ng/ml |
| 8 mg | 2.3-3.8 ng/ml | 22.7-34.1 hr · ng/ml |
| 12 mg | 2.8-5.2 ng/ml | 30.4-48.6 hr · ng/ml |
| 16 mg | 4.08-6.4 ng/ml | 42.6-65.8 hr · ng/ml |

Example 6

Preparation of Films for In Vivo Study

Film dosages were prepared for use in an in vivo study to determine the bioavailability of buprenorphine/naloxone tablets and film formulations. Specifically, the films were tested to determine whether the film provides a bioequivalent effect to that of a tablet formulation.

Three film formulations including 8 mg buprenorphine and 2 mg naloxone were prepared, each being buffered to a different pH. The first film did not include any buffer, providing a local pH of about 6.5. The second was buffered to a local pH level of about 3-3.5. The third was buffered to a local pH value of about 5-5.5. The formulations are set forth in Table 6 below.

TABLE 6

Formulations of Test Films at Various pH Levels

| | Test formulation 1 8 mg/2 mg pH = 6.5 | | Test formulation 2 8 mg/2 mg pH = 3-3.5 | | Test formulation 3 8 mg/2 mg pH = 5-5.5 | |
|---|---|---|---|---|---|---|
| Component | % w/w | Mg/ film | % w/w | Mg/ film | % w/w | Mg/ film |
| Buprenorphine HCl | 21.61 | 8.64 | 17.28 | 8.64 | 17.28 | 8.64 |
| Naloxone HCl Dihydrate | 6.10 | 2.44 | 4.88 | 2.44 | 4.88 | 2.44 |
| Polymer | 5.05 | 2.02 | 4.82 | 2.41 | 4.82 | 2.41 |
| Polymer | 28.48 | 11.39 | 27.09 | 13.55 | 27.09 | 13.55 |
| Polymer | 12.65 | 5.06 | 12.04 | 6.02 | 12.04 | 6.02 |
| Polymer | 4.43 | 1.77 | 4.22 | 2.11 | 4.22 | 2.11 |
| Sweetener | 12.65 | 5.06 | 12.04 | 6.02 | 12.04 | 6.02 |
| Sweetener | 3 | 1.2 | 3 | 1.5 | 3 | 1.5 |
| Flavor | 6 | 2.4 | 6 | 3 | 6 | 3 |
| Citric acid | 0 | 0 | 5.92 | 2.96 | 2.51 | 1.26 |
| Sodium citrate | 0 | 0 | 2.68 | 1.34 | 6.08 | 3.04 |
| FD&C yellow #6 | 0.025 | 0.01 | 0.03 | 0.02 | 0.03 | 0.02 |
| Total | 100 | 40 | 100 | 50 | 100 | 50 |

Example 7

Analysis of In Vivo Absorption of Film Having a pH of 6.5

The film dosage composition of film having a local pH of 6.5 was analyzed. Specifically, Test Formulation 1, as prepared in Example 5 was analyzed in vivo to determine the absorption of buprenorphine and of naloxone. The comparative film was compared to the absorption of buprenorphine and of naloxone provided by a one dose tablet (Suboxone®). The test film was compared to determine whether it provided a bioequivalent effect as the Suboxone® tablet.

The results for Test Formulation 1, which had a local pH of about 6.5, as compared to the one dose tablet, are set forth in Tables 7 and 8 below.

TABLE 7

Buprenorphine In Vivo Absorption Data for Test Formulation 1

| | Suboxone ® sublingual | | | | Test Formulation 1 (pH = 6.5) | | | |
|---|---|---|---|---|---|---|---|---|
| Parameter | n | Mean | SD | CV % | n | Mean | SD | CV % |
| $T_{max}$ (hr) | 15 | 1.60 | 0.47 | 29.41 | 15 | 1.50 | 0.62 | 41.23 |
| $C_{max}$ (ng/mL) | 15 | 2.27 | 0.562 | 24.77 | 15 | 2.60 | 0.872 | 33.53 |
| $AUC_{last}$ (hr*ng/ mL) | 15 | 27.08 | 10.40 | 38.41 | 15 | 31.00 | 12.93 | 41.72 |

TABLE 7-continued

Buprenorphine In Vivo Absorption Data for Test Formulation 1

| Parameter | Suboxone ® sublingual | | | | Test Formulation 1 (pH = 6.5) | | | |
|---|---|---|---|---|---|---|---|---|
| | n | Mean | SD | CV % | n | Mean | SD | CV % |
| $AUC_{inf}$ (hr*ng/mL) | 15 | 29.58 | 11.15 | 37.68 | 15 | 33.37 | 13.88 | 41.61 |
| $T_{1/2}$ (hr) | 15 | 44.76 | 20.86 | 46.60 | 15 | 40.73 | 14.93 | 36.66 |

TABLE 8

Naloxone In Vivo Absorption Data for Test Formulation 1

| Parameter | Suboxone ® sublingual | | | | Test Formulation 1 (pH = 6.5) | | | |
|---|---|---|---|---|---|---|---|---|
| | n | Mean | SD | CV % | n | Mean | SD | CV % |
| $T_{max}$ (hr) | 15 | 0.90 | 0.23 | 25.32 | 15 | 0.68 | 0.18 | 25.75 |
| $C_{max}$ (pg/mL) | 15 | 94.6 | 39.1 | 41.33 | 15 | 410 | 122 | 29.75 |
| $AUC_{last}$ (hr*pg/mL) | 15 | 297.1 | 120.7 | 40.62 | 15 | 914.8 | 158.1 | 17.29 |
| $AUC_{inf}$ (hr*pg/mL) | 15 | 306.1 | 122.6 | 40.06 | 15 | 924.2 | 158.8 | 17.18 |
| $T_{1/2}$ (hr) | 15 | 6.62 | 2.60 | 39.26 | 15 | 6.86 | 2.08 | 30.27 |

As can be seen, the in vivo data indicates that buprenorphine is absorbed very well from the film formulation at a local pH of 6.5, and matched closely the absorption seen in the Suboxone® one dose tablet. However, the absorption was also maximized for the naloxone, which was undesirable. It was determined that a film having a combination of buprenorphine and naloxone and a local pH of 6.5 did not provide a bioequivalent effect as the one dose Suboxone® tablet for both buprenorphine and naloxone.

Example 8

Analysis of In Vivo Absorption of Film Having a pH of 5-5.5

Having determined the absorption of buprenorphine and naloxone in film having a local pH of 6.5, a film dosage composition of film having a local pH of 5-5.5 was analyzed. Specifically, Test Formulation 3, as prepared in Example 5 was analyzed in vivo to determine the absorption of buprenorphine and of naloxone. The comparative films were compared to the absorption of buprenorphine and of naloxone provided by a one dose tablet (Suboxone®). The test film was compared to determine whether it provided a bioequivalent effect as the tablet product.

The results for Test Formulation 3, which had a local pH of about 5-5.5, as compared to the one dose tablet, are set forth in Tables 9 and 10 below.

TABLE 9

Buprenorphine In Vivo Absorption Data for Test Formulation 3

| Parameter | Suboxone ® sublingual | | | | Test Formulation 3 (pH = 5-5.5) | | | |
|---|---|---|---|---|---|---|---|---|
| | n | Mean | SD | CV % | n | Mean | SD | CV % |
| $T_{max}$ (hr) | 15 | 1.60 | 0.47 | 29.41 | 14 | 1.50 | 0.43 | 28.50 |
| $C_{max}$ (ng/mL) | 15 | 2.27 | 0.562 | 24.77 | 14 | 3.47 | 1.57 | 45.40 |
| $AUC_{last}$ (hr*ng/mL) | 15 | 27.08 | 10.40 | 38.41 | 14 | 33.25 | 16.01 | 48.16 |
| $AUC_{inf}$ (hr*ng/mL) | 15 | 29.58 | 11.15 | 37.68 | 13 | 38.34 | 15.38 | 40.13 |
| $T_{1/2}$ (hr) | 15 | 44.76 | 20.86 | 46.60 | 13 | 41.71 | 17.70 | 42.42 |

TABLE 10

Naloxone In Vivo Absorption Data for Test Formulation 3

| Parameter | Suboxone ® sublingual | | | | Test Formulation 3 (pH = 5-5.5) | | | |
|---|---|---|---|---|---|---|---|---|
| | n | Mean | SD | CV % | n | Mean | SD | CV % |
| $T_{max}$ (hr) | 15 | 0.90 | 0.23 | 25.32 | 14 | 0.98 | 0.62 | 63.51 |
| $C_{max}$ (pg/mL) | 15 | 94.6 | 39.1 | 41.33 | 14 | 173 | 84.5 | 48.79 |
| $AUC_{last}$ (hr*pg/mL) | 15 | 297.1 | 120.7 | 40.62 | 14 | 455.2 | 195.5 | 42.94 |
| $AUC_{inf}$ (hr*pg/mL) | 15 | 306.1 | 122.6 | 40.06 | 13 | 474.4 | 203.1 | 42.81 |
| $T_{1/2}$ (hr) | 15 | 6.62 | 2.60 | 39.26 | 13 | 9.45 | 6.90 | 73.00 |

As can be seen, the in vivo data indicated that the absorption of buprenorphine increased as the local pH level decreased. It appeared that by decreasing the local pH from 6.5 to 5.5, the absorption of buprenorphine was being moved to a level much greater than that of the one dose Suboxone® tablet. In addition, the naloxone values did not provide a bioequivalent result as the one dose tablet. Thus, it was determined that the film having a local pH of 5.5 did not provide a bioequivalent result as that of the Suboxone® tablet for both buprenorphine and naloxone.

It was noted that by reducing the local pH of the film to a level of 5.5, there would be provided an increased level of absorption of buprenorphine. Thus, it may be desirable to buffer a film composition incorporating buprenorphine itself to a level of about 5.5 to provide an increased absorption.

Example 9

Analysis of In Vivo Absorption of Film Having a pH of 3-3.5

Having determined the absorption of buprenorphine and naloxone in films having a local pH of 6.5 and 5.5, a film dosage composition of film having a local pH of about 3-3.5 was analyzed. It was assumed that the absorption of buprenorphine would continue to be increased as it had demonstrated at a local pH of 5.5. Thus, it was assumed that at a local pH of 3.5, the film would not be bioequivalent to that of the tablet.

Specifically, Test Formulation 2, as prepared in Example 5, was analyzed in vivo to determine the absorption of buprenorphine and of naloxone. The comparative films were compared to the absorption of buprenorphine and of naloxone provided by a one dose tablet (Suboxone®). The test film was compared to determine whether it provided a bioequivalent effect as the tablet product.

The results for Test Formulation 2, which had a local pH of about 3-3.5, as compared to the one dose tablet, are set forth in Tables 11 and 12 below.

TABLE 11

Buprenorphine In Vivo Absorption Data for Test Formulation 2

| | Suboxone ® sublingual | | | Test Formulation 2 (pH = 3-3.5) | | | |
|---|---|---|---|---|---|---|---|
| Parameter | n | Mean | SD | CV % | n | Mean | SD | CV % |
| $T_{max}$ (hr) | 15 | 1.60 | 0.47 | 29.41 | 14 | 1.68 | 0.58 | 34.68 |
| $C_{max}$ (ng/mL) | 15 | 2.27 | 0.562 | 24.77 | 14 | 2.68 | 0.910 | 33.99 |
| $AUC_{last}$ (hr*ng/mL) | 15 | 27.08 | 10.40 | 38.41 | 14 | 29.73 | 12.05 | 40.54 |
| $AUC_{inf}$ (hr*ng/mL) | 15 | 29.58 | 11.15 | 37.68 | 14 | 31.45 | 12.98 | 41.26 |
| $T_{1/2}$ (hr) | 15 | 44.76 | 20.86 | 46.60 | 14 | 30.03 | 13.95 | 46.46 |

TABLE 12

Naloxone In Vivo Absorption Data for Test Formulation 2

| | Suboxone ® sublingual | | | | Test Formulation 2 (pH = 3-3.5) | | | |
|---|---|---|---|---|---|---|---|---|
| Parameter | n | Mean | SD | CV % | n | Mean | SD | CV % |
| $T_{max}$ (hr) | 15 | 0.90 | 0.23 | 25.32 | 14 | 0.84 | 0.19 | 22.19 |
| $C_{max}$ (pg/mL) | 15 | 94.6 | 39.1 | 41.33 | 14 | 130 | 72.9 | 56.04 |
| $AUC_{last}$ (hr*pg/mL) | 15 | 297.1 | 120.7 | 40.62 | 14 | 362.2 | 155.9 | 43.03 |
| $AUC_{inf}$ (hr*pg/mL) | 15 | 306.1 | 122.6 | 40.06 | 12 | 350.4 | 142.3 | 40.61 |
| $T_{1/2}$ (hr) | 15 | 6.62 | 2.60 | 39.26 | 12 | 8.07 | 4.75 | 58.84 |

As can be seen, the in vivo data indicated that the absorption of buprenorphine was substantially bioequivalent to that of the one dose tablet when the film composition local pH was lowered to about 3-3.5. This result was surprising as it did not appear to follow the pH partition theory. Further, at a local pH of about 3-3.5, it was seen that the absorption of naloxone was substantially bioequivalent to that of the one dose tablet.

Thus, it was determined that the film product including buprenorphine and naloxone at a local pH of 3-3.5 was substantially bioequivalent to that of the Suboxone® one dose tablet. It was therefore evident that one could formulate the naloxone at a local pH of 3.5 or lower to inhibit its absorption, and formulate the buprenorphine at a local pH of about 5.5 to optimize its absorption.

Example 10

Normalized Values for Naloxone in Films and Tablets

Various film compositions including buprenorphine and naloxone in 8/2 mg and 2/0.5 mg dosages, and having different local pH values from 6.5 to 3.5, were prepared and analyzed. The data was normalized and compared to the one dose Suboxone® tablet. The results are set forth in Table 13 below.

TABLE 13

Normalized Values for Naloxone Film Compared to Tablet

| pH | Dose (mg) Buprenorphine/ Naloxone | AUC (Normalized) | Cmax | Mg Citric Acid | Ratio Citric Acid (mg)/Naloxone (mg) |
|---|---|---|---|---|---|
| 6.5 | 8/2 | 3.02 | 4.33 | 1.34 | 0.67 |
| 5.5 | 8/2 | 1.55 | 1.83 | 1.34 | 0.67 |
| 3.5 | 8/2 | 1.14 | 1.37 | 1.34 | 0.67 |
| 3.5 | 2/0.5 | 0.98 | 0.90 | 1.34 | 2.68 |
| 5.5 | 2/0.5 | 1.41 | 1.41 | 1.34 | 2.68 |

The data indicates that not only is the local pH of significant importance, but the amount of acid present in the formula is also important. The improvement from the 8/2 dose to the 2/0.5 dose (at a local pH of 3.5) demonstrates this importance. The 8/2 dose has a ratio of acid/naloxone of 0.67, and this dose provided borderline acceptable bioequivalent results. In contrast, the 2/0.5 dose has a ratio of acid/naloxone of 2.68 at a local pH of 3.5, and provides a more bioequivalent absorption value than the 8/2 dose.

In fact, the data shows that the 2/0.5 dose at a local pH of 3.5 had an even lower buccal absorption than the one dose tablet, as seen from the normalized values for the AUC and Cmax. This demonstrates that even less absorption of the naloxone occurs for the film formulation at a local pH of 3.5 than the tablet formulation. Given the goal of reducing the absorption of naloxone, it appears that the film product buffered at a local pH of 3.5 with a buffer ratio (buffer/naloxone) of 2.68 provides even better results than the Suboxone® formulation.

Example 11

Absorption Data for Dual-Film Dosage at Local pH 3.5 and Local pH 5.5

A dual-film dosage is prepared, with the first film layer having a local pH of about 3.5 and containing an antagonist therein, and the second film layer having a local pH of about 5.5 and containing an agonist therein. In this dual-film dosage, the first film layer (having the antagonist) is a fast-dissolving film, while the second film layer (having the agonist) is a moderate dissolving film. Using data from the above studies, absorption levels for various amounts of product in the film is presented in Table 14 below:

TABLE 14

Extrapolated Absorption Data for Dual-Layered Film at Agonist Local pH of 3.5 and Naloxone Local pH of 5.5

| Dose (mg agonist/ mg naloxone) | Naloxone Cmax (pg/ml) | Naloxone AUC (hr * pg/ml) |
|---|---|---|
| 2/0.5 | 32.5 | 90.5 |
| 8/2 | 130 | 362 |
| 16/4 | 260 | 724 |

Therefore, at amounts of 0.5-4.0 mg, the Cmax level for the Naloxone is between about 32.5 to about 260 pg/ml and the AUC for the Naloxone is between about 90.5 to about 724 hr*pg/ml. As will be understood, varying types and levels of buffers may increase or decrease the absorption values. That is, when seeking to inhibit the absorption of the antagonist (i.e., naloxone), one may select a particular local pH for the agonist region and a second local pH for the antagonist region. The local pH of the region may depend on the amount of active included in that region. The amounts of actives incorporated into the dosage may be altered to provide suitable absorption levels, and may include amounts in milligrams, nanograms, picograms, or any desired amount of active.

Example 12

Comparison of Antioxidants and Stabilizing Agents on the Stability of Naloxone in a 8/2 mg (Buprenorphine/Naloxone) Film Formulation Lab scale batches of 8/2 mg (Buprenorphine/Naloxone) film dosage units containing the following excipients were produced as previously described:
1. Ascorbic Acid
2. EDTA (Ethylenediaminetetraacetic Acid Disodium Salt)
3. BHT (Butylated Hydroxytoluene)
4. Propyl Gallate
5. Sodium sulfite
6. Citric Acid
7. Sodium Metabisulfite
8. Stabilizer System containing Ascorbic Acid, EDTA, Sodium metabisulfite, BHT.

Samples were stored for 4 weeks at 60° C. and a relative humidity of 57%. The amounts of naloxone and oxidation products of naloxone, 5-hydroxy naloxone (5HN), naloxone n-oxide (NNO), and noroxymorphone (NOMP) were then determined. The results are reported in Table 15:

TABLE 15

4 Week Stability Naloxone/Antioxidant Study

| Sample | No. | % Naloxone Initial | % Naloxone 4 Weeks | % 5HN Initial | % 5HN 4 Weeks | % NNO Initial | % NNO 4 Weeks | % NOMP Initial | % NOMP 4 Weeks |
|---|---|---|---|---|---|---|---|---|---|
| Control | | 109.9 | 101.2 | 0.1723 | 0.910 | 0.0260 | ND | 0.1358 | 0.64 |
| Ascorbic Acid | 1 | 104.7 | 94.3 | 0.0908 | 0.44 | ND | ND | 0.1115 | 0.16 |
| EDTA | 2 | 105.6 | 102.0 | 0.0385 | 0.18 | 0.0028 | ND | 0.1262 | 0.17 |
| BHT | 3 | 105.3 | 100.4 | 0.0906 | 0.86 | ND | ND | 0.1365 | 0.30 |
| Propyl Gallate | 4 | 102.6 | 97.7 | 0.3057 | 0.90 | ND | ND | 0.1565 | 0.25 |
| Na Sulfite | 5 | 104.7 | 98.1 | 0.0991 | 1.14 | 0.0035 | ND | 0.1318 | 0.53 |
| Citric Acid | 6 | 105.1 | 98.1 | 0.1208 | 1.38 | ND | ND | 0.1374 | 0.66 |
| Na Metabi-Sulfite | 7 | 64.2 | 55.8 | 0.0395 | 0.12 | ND | ND | 0.3855 | 2.47 |
| Stabilizer System | 8 | 112.3 | 105.1 | 0.0466 | 0.01 | ND | ND | 0.1482 | 0.91 |

The addition of the stabilizer system and EDTA had a positive impact on the production of 5HN. The addition of sodium sulfite, BHT, citric acid and propyl gallate had no improvement over control.

The addition of EDTA results in a reduction of 5HN from 0.91% to 0.18% after 4 weeks storage at 60° C. and 75% relative humidity. Thus, EDTA appears to be effective in stabilizing naloxone in the film compositions.

Example 13

EDTA Concentration Study

The appropriate EDTA level to protect naloxone from oxidation when used in the formulation of the 8/2 mg (buprenorphine/naloxone) film was studied. Samples of the 8/2 mg (buprenorphine/naloxone) films were produced with following amounts of EDTA: 4.0 mg, 2.0 mg, 1.0 mg, 0.2 mg, and no EDTA (control).

The samples were stored at 60° C. and 75% relative humidity for 4 weeks and the combined content of 2 primary oxidation product, 5HN and NNO was determined initially, at 2 weeks, and at 4 weeks for each formula. The results are reported in FIG. 1.

Based on the incremental differences observed in the summed levels of 5HN and NNO between the 2 mg EDTA sample and the 1 mg EDTA sample, a 1 mg level of EDTA is sufficient to significantly reduce oxidation of naloxone in the film product.

What is claimed is:
1. A drug delivery composition for making a plurality of individual unit doses in a self-supporting film dosage form, which plurality of individual unit doses being cut from a self-supporting film not made in a mold or well having at least one particulate active substantially uniformly stationed in said film, each of said individual unit doses containing a desired amount of said at least one particulate active, said composition comprising:
 a. a polymeric carrier matrix comprising polyethylene oxide and polyvinylpyrrolidone;
 b. naloxone or a pharmaceutical salt thereof;
 c. the at least one particulate active selected from the group consisting of analgesics, narcotics, opiates, and opiate derivatives;
 d. citric acid;
 e. an antioxidant;
 f. a sweetener selected from the group consisting of acesulfame potassium salt, sodium saccharin, sucralose, aspartame and combinations thereof;
 g. at least one coloring agent selected from the group consisting of FD&C colors, D&C colors, and combinations thereof;
 h. at least one flavor;
 i. a hydrogenated starch hydrolysate; and
 j. disodium phosphate, wherein said uniformity of the film from which the plurality of individual unit doses is cut is measured by substantially equally sized individual unit doses cut from the film which do not vary by more than 10% of a desired amount of said at least one particulate active.

2. The composition of claim 1, further comprising propylene glycol, shellac, or a combination thereof.

3. The composition of claim 1, wherein the antioxidant is selected from the group consisting of BHT, BHA, citric acid, propyl gallate, sodium sulfate, sodium metabisulfite, ascorbic acid, tocopherol, tocopherol ester derivatives, 2-mercaptobenzimidazole, and combinations thereof.

4. The composition of claim 1, wherein the at least one flavor comprises a lemon-lime flavor.

5. The composition of claim 1, wherein the at least one flavor comprises a component selected from the group consisting of alpha-citral, beta-citral, decanal, aldehyde C-8, aldehyde C-9, aldehyde C-12, and combinations thereof.

6. The composition of claim 1, wherein the polymeric carrier matrix further comprises silicon dioxide.

7. A drug delivery composition for making a plurality of individual unit doses in a self-supporting film dosage form, which plurality of individual unit doses being cut from a self-supporting film not made in a mold or well having at least one particulate active substantially uniformly stationed in said film, each of said individual unit doses containing a desired amount of said at least one particulate active, said composition comprising:
  a. a polymeric carrier matrix comprising a component selected from the group consisting of polyethylene oxide, polyvinylpyrrolidone, cellulose, a cellulose derivative, polyvinyl alcohol, a polysaccharide, and combinations thereof;
  b. naloxone or a pharmaceutical salt thereof;
  c. the at least one particulate active selected from the group consisting of analgesics, narcotics, opiates, and opiate derivatives;
  d. a buffering agent;
  e. an antioxidant;
  f. an artificial sweetener;
  g. at least one coloring agent selected from FD&C colors, D&C colors and combinations thereof; and
  h. at least one flavor,
wherein said uniformity of the film from which the plurality of individual unit doses is cut is measured by substantially equally sized individual unit doses cut from the film which do not vary by more than 10% of a desired amount of said at least one particulate active and
wherein said uniformity of the film is maintained by preventing surface skinning prior to drying the depth of said film.

8. The composition of claim 7, wherein the antioxidant is selected from the group consisting of BHT, BHA, citric acid, propyl gallate, sodium sulfate, sodium metabisulfite, ascorbic acid, tocopherol, tocopherol ester derivatives, 2-mercaptobenzimidazole, and combinations thereof.

9. The composition of claim 7, wherein the at least one flavor comprises a lemon-lime flavor.

10. The composition of claim 7, wherein the at least one flavor comprises a component selected from the group consisting of alpha-citral, beta-citral, decanal, aldehyde C-8, aldehyde C-9, aldehyde C-12, and combinations thereof.

11. The composition of claim 7, further comprising shellac.

12. The composition of claim 7, wherein the polymeric carrier matrix further comprises silicon dioxide.

13. A drug delivery composition for making a plurality of individual unit doses in a self-supporting film dosage form, which plurality of individual unit doses being cut from a self-supporting conveyed film having at least one particulate active substantially uniformly stationed in said conveyed film, each of said individual unit doses containing a desired amount of said at least one particulate active, said composition comprising:
  a. a polymeric carrier matrix comprising polyethylene oxide and polyvinylpyrrolidone;
  b. naloxone or a pharmaceutical salt thereof;
  c. the at least one particulate active selected from the group consisting of analgesics, narcotics, opiates, and opiate derivatives;
  d. citric acid;
  e. an antioxidant;
  f. a sweetener selected from the group consisting of acesulfame potassium salt, sodium saccharin, sucralose, aspartame and combinations thereof;
  g. at least one coloring agent selected from the group consisting of FD&C colors, D&C colors, and combinations thereof;
  h. at least one flavor;
  i. a hydrogenated starch hydrolysate; and
  j. disodium phosphate,
wherein said uniformity of the conveyed film from which the plurality of individual unit doses is cut is measured by substantially equally sized individual unit doses cut from the conveyed film which do not vary by more than 10% of a desired amount of said at least one particulate active.

14. The composition of claim 13, further comprising propylene glycol, shellac, or a combination thereof.

15. The composition of claim 13, wherein the antioxidant is selected from the group consisting of BHT, BHA, citric acid, propyl gallate, sodium sulfate, sodium metabisulfite, ascorbic acid, tocopherol, tocopherol ester derivatives, 2-mercaptobenzimidazole, and combinations thereof.

16. The composition of claim 13, wherein the at least one flavor comprises a lemon-lime flavor.

17. The composition of claim 13, wherein the at least one flavor comprises a component selected from the group consisting of alpha-citral, beta-citral, decanal, aldehyde C-8, aldehyde C-9, aldehyde C-12, and combinations thereof.

18. The composition of claim 13, wherein the polymeric carrier matrix further comprises silicon dioxide.

19. A drug delivery composition for making a plurality of individual unit doses in a self-supporting film dosage form, which plurality of individual unit doses being cut from a self-supporting film having at least one particulate active substantially uniformly stationed in said film, each of said individual unit doses containing a desired amount of said at least one particulate active, said composition comprising:
  a. a polymeric carrier matrix comprising a component selected from the group consisting of polyethylene oxide, polyvinylpyrrolidone, cellulose, a cellulose derivative, polyvinyl alcohol, a polysaccharide, and combinations thereof;
  b. naloxone or a pharmaceutical salt thereof;
  c. the at least one particulate active selected from the group consisting of analgesics, narcotics, opiates, and opiate derivatives;
  d. a buffering agent;
  e. an antioxidant;
  f. an artificial sweetener;
  g. at least one coloring agent selected from FD&C colors, D&C colors and combinations thereof; and
  h. at least one flavor, wherein said uniformity of the film from which the plurality of individual unit doses is cut is measured by substantially equally sized individual unit doses cut from the film which do not vary by more than 10% of a desired amount of said at least one particulate active.

20. The composition of claim 19, wherein the antioxidant is selected from the group consisting of BHT, BHA, citric acid, propyl gallate, sodium sulfate, sodium metabisulfite, ascorbic acid, tocopherol, tocopherol ester derivatives, 2-mercaptobenzimidazole, and combinations thereof.

21. The composition of claim 19, wherein the at least one flavor comprises a lemon-lime flavor.

22. The composition of claim 19, wherein the at least one flavor comprises a component selected from the group consisting of alpha-citral, beta-citral, decanal, aldehyde C-8, aldehyde C-9, aldehyde C-12, and combinations thereof.

23. The composition of claim 19, further comprising shellac.

24. The composition of claim 19, wherein the polymeric carrier matrix further comprises silicon dioxide.

25. The composition of claim 1, wherein said uniformity of the film is maintained by preventing surface skinning prior to drying the depth of said film using a conventional drying method.

26. The composition of claim 25, wherein said uniformity of the film is maintained by using a viscosity that maintains a non-self-aggregating uniform heterogeneity of said film or prevents rippling.

27. The composition of claim 7, wherein said uniformity of the film is maintained by preventing surface skinning prior to drying the depth of said film using a conventional drying method.

28. The composition of claim 27, wherein said uniformity of the film is maintained by using a viscosity that maintains a non-self-aggregating uniform heterogeneity of said film or prevents rippling.

29. The composition of claim 13, wherein said uniformity of the film is maintained by preventing surface skinning prior to drying the depth of said film using a conventional drying method.

30. The composition of claim 19, wherein said uniformity of the film is maintained by preventing surface skinning prior to drying the depth of said film using a conventional drying method.

* * * * *